United States Patent [19]
Bridon et al.

[11] Patent Number: 6,087,375
[45] Date of Patent: Jul. 11, 2000

[54] METHODS OF TREATING OR PREVENTING THROMBOSES

[75] Inventors: Dominique P. Bridon, Outremont, Canada; Alan Ezrin, Moraga; Peter Milner, Los Altos Hills, both of Calif.

[73] Assignee: ConjuChem, Inc., Montreal, Canada

[21] Appl. No.: 09/330,744

[22] Filed: Jun. 11, 1999

Related U.S. Application Data

[63] Continuation of application No. 09/108,534, Jul. 1, 1998, Pat. No. 5,942,620, which is a continuation of application No. 08/674,315, Jul. 1, 1996, Pat. No. 5,840,733.

[51] Int. Cl.⁷ .................. C07D 215/04; C07D 215/06; A61K 31/4709
[52] U.S. Cl. .......................................... 514/314; 546/166
[58] Field of Search .............................. 514/314; 546/166

[56] References Cited

U.S. PATENT DOCUMENTS

| | | | |
|---|---|---|---|
| 3,622,615 | 11/1971 | Nicolaides et al. | 260/470 |
| 3,978,045 | 8/1976 | Okamoto et al. | 260/239 |
| 3,992,530 | 11/1976 | Foell et al. | 424/177 |
| 4,018,913 | 4/1977 | Okamoto et al. | 424/177 |
| 4,018,915 | 4/1977 | Okamoto et al. | 424/177 |
| 4,036,955 | 7/1977 | Okamoto et al. | 424/177 |
| 4,041,156 | 8/1977 | Okamoto et al. | 424/177 |
| 4,046,876 | 9/1977 | Okamoto et al. | 424/177 |
| 4,049,645 | 9/1977 | Okamoto et al. | 260/239 |
| 4,055,636 | 10/1977 | Okamoto et al. | 424/177 |
| 4,055,651 | 10/1977 | Okamoto et al. | 424/267 |
| 4,062,963 | 12/1977 | Okamoto et al. | 424/267 |
| 4,066,758 | 1/1978 | Okamoto et al. | 424/244 |
| 4,066,759 | 1/1978 | Okamoto et al. | 424/244 |
| 4,066,773 | 1/1978 | Okamoto et al. | 424/267 |
| 4,069,317 | 1/1978 | Okamoto et al. | 424/177 |
| 4,069,318 | 1/1978 | Okamoto et al. | 424/177 |
| 4,069,323 | 1/1978 | Okamoto et al. | 424/244 |
| 4,069,329 | 1/1978 | Okamoto et al. | 424/267 |
| 4,070,457 | 1/1978 | Okamoto et al. | 424/177 |
| 4,071,621 | 1/1978 | Okamoto et al. | 424/177 |
| 4,072,743 | 2/1978 | Okamoto et al. | 424/177 |
| 4,072,744 | 2/1978 | Okamoto et al. | 424/177 |
| 4,072,757 | 2/1978 | Okamoto et al. | 424/267 |
| 4,073,891 | 2/1978 | Okamoto et al. | 242/177 |
| 4,073,892 | 2/1978 | Okamoto et al. | 424/177 |
| 4,073,913 | 2/1978 | Okamoto et al. | 424/267 |
| 4,073,914 | 2/1978 | Kikumoto et al. | 424/267 |
| 4,073,916 | 2/1978 | Okamoto et al. | 424/267 |
| 4,093,712 | 6/1978 | Okamoto et al. | 424/177 |
| 4,096,255 | 6/1978 | Kikumoto et al. | 424/246 |
| 4,097,472 | 6/1978 | Okamoto et al. | 424/177 |
| 4,097,591 | 6/1978 | Okamoto et al. | 424/177 |
| 4,101,653 | 7/1978 | Okamoto et al. | 424/177 |
| 4,104,392 | 8/1978 | Okamoto et al. | 424/258 |
| 4,108,986 | 8/1978 | Okamoto et al. | 424/177 |
| 4,117,127 | 9/1978 | Okamoto et al. | 424/247 |
| 4,125,604 | 11/1978 | Okamoto et al. | 424/177 |
| 4,125,619 | 11/1978 | Okamoto et al. | 424/267 |
| 4,131,673 | 12/1978 | Okamoto et al. | 424/247 |
| 4,133,880 | 1/1979 | Okamoto et al. | 424/244 |
| 4,139,529 | 2/1979 | Okamoto et al. | 260/239 |
| 4,140,681 | 2/1979 | Okamoto et al. | 260/112.5 R |
| 4,154,828 | 5/1979 | Okamoto et al. | 424/244 |
| 4,168,307 | 9/1979 | Okamoto et al. | 424/244 |

(List continued on next page.)

FOREIGN PATENT DOCUMENTS

| | | | |
|---|---|---|---|
| 0 008 746 A1 | 3/1980 | European Pat. Off. | C07D 401/12 |
| 0 181 267 A2 | 5/1986 | European Pat. Off. | A61K 37/02 |
| 0 395 918 A2 | 11/1990 | European Pat. Off. | C12N 11/02 |
| 0 602 290 A1 | 6/1994 | European Pat. Off. | A61K 47/48 |
| 0 608 828 A1 | 8/1994 | European Pat. Off. | A61K 31/47 |
| 0 614 986 A1 | 9/1994 | European Pat. Off. | C12P 41/00 |
| 0 669 131 A1 | 8/1995 | European Pat. Off. | A61K 31/47 |
| 0 686 642 A2 | 10/1996 | European Pat. Off. . | |
| 44 24 828 A1 | 1/1996 | Germany . | |
| WO 90/11783 | 10/1990 | WIPO | A61K 47/48 |
| WO 90/12585 | 11/1990 | WIPO | A61K 37/00 |
| WO 91/02750 | 3/1991 | WIPO | C07K 7/10 |
| WO 92/00091 | 1/1992 | WIPO | A61K 37/02 |
| WO 92/02560 | 2/1992 | WIPO | C08F 2/38 |
| WO 92/13952 | 8/1992 | WIPO | C12N 15/15 |
| WO 93/25217 | 12/1993 | WIPO | A61K 37/00 |
| WO 94/09034 | 4/1994 | WIPO | C07K 13/00 |
| WO 95/10302 | 4/1995 | WIPO | A61K 39/395 |
| WO 95/18623 | 7/1995 | WIPO | A61K 31/74 |
| WO 96/06626 | 3/1996 | WIPO | A61K 38/00 |
| WO 96/15774 | 5/1996 | WIPO | A61K 9/127 |
| WO 97/25074 | 7/1997 | WIPO | A61K 49/00 |
| WO 98/11437 | 3/1998 | WIPO | G01N 33/53 |

OTHER PUBLICATIONS

Bagdanov, et al., Long–Circulating Blood Pool Imaging Agents, Advanced Drug Delivery Reviews 16:335–48 (1995).

Brummel, et al., A Mass Spectrometric Solution to the Address Problem of Combinatorial Libraries, Science 264:399–401 (1994).

Gordon, et al., Applications of Combinatorial Technologies to Drug Discovery. 2. Combinatorial Organic Synthesis, Library Screening Strategies, and Future Directions, J. Med. Chem. 37(10):1385–1401 (1994).

(List continued on next page.)

*Primary Examiner*—D. Margaret Seaman
*Attorney, Agent, or Firm*—Limbach & Limbach LLP

[57] ABSTRACT

Novel compounds comprising chemically reactive intermediates which can react with available reactive functionalities on blood components to form covalent linkages, where the resulting covalently-bound conjugates are found to have thrombin inhibition activity are provided. Specifically, the thrombin inhibitor compounds of the present invention are derivatives of the known thrombin inhibitor argatroban, which can be covalently linked to chemically reactive functionalities on various blood components. The conjugated thrombin inhibitors thereby have extended lifetimes in the bloodstream, as compared to the unconjugated parent drug, and are, therefore, capable of maintaining thrombin inhibitory activity for extended periods of time as compared to the unconjugated parent drug. Also provided herein are methods for inhibiting thrombin activity in vivo comprising administering to the bloodstream of a mammalian host the novel compounds of the present invention.

23 Claims, 11 Drawing Sheets

U.S. PATENT DOCUMENTS

| | | | |
|---|---|---|---|
| 4,173,630 | 11/1979 | Okamoto et al. | 424/177 |
| 4,201,863 | 5/1980 | Okamoto et al. | 546/166 |
| 4,258,192 | 3/1981 | Okamoto et al. | 546/166 |
| 4,537,896 | 8/1985 | Claeson et al. | 514/330 |
| 4,816,560 | 3/1989 | Verdini et al. | 530/323 |
| 4,822,788 | 4/1989 | Kishimoto et al. | 514/210 |
| 4,977,168 | 12/1990 | Bernat et al. | 514/330 |
| 5,122,615 | 6/1992 | Ito et al. | 424/426 |
| 5,141,947 | 8/1992 | Tamao | 514/314 |
| 5,196,404 | 3/1993 | Maraganore et al. | 514/13 |
| 5,240,913 | 8/1993 | Maraganore et al. | 514/13 |
| 5,242,810 | 9/1993 | Maraganore et al. | 435/69.2 |
| 5,274,098 | 12/1993 | Stiier et al. | 546/226 |
| 5,332,822 | 7/1994 | Misra | 546/164 |
| 5,371,091 | 12/1994 | Misra et al. | 514/314 |
| 5,424,291 | 6/1995 | Atrash et al. | 514/18 |
| 5,457,114 | 10/1995 | Stuber et al. | 514/319 |
| 5,458,568 | 10/1995 | Racchini et al. | 604/19 |
| 5,484,772 | 1/1996 | Sall et al. | 514/18 |
| 5,488,037 | 1/1996 | Sall et al. | 514/19 |
| 5,492,895 | 2/1996 | Vlasuk et al. | 514/18 |
| 5,506,241 | 4/1996 | Mano et al. | 514/317 |
| 5,510,330 | 4/1996 | Martin et al. | 514/12 |
| 5,514,409 | 5/1996 | Maraganore et al. | 427/2.24 |
| 5,552,410 | 9/1996 | Galtier et al. | 514/311 |
| 5,558,642 | 9/1996 | Schweich et al. | 604/96 |
| 5,559,150 | 9/1996 | Soll | 514/562 |
| 5,561,146 | 10/1996 | Kim | 514/326 |
| 5,565,471 | 10/1996 | Ozaki | 514/312 |
| 5,571,844 | 11/1996 | Stuber et al. | 514/602 |
| 5,578,594 | 11/1996 | Ackermann et al. | 514/236.2 |
| 5,583,113 | 12/1996 | Berry et al. | 514/18 |
| 5,583,146 | 12/1996 | Kimball et al. | 514/326 |
| 5,588,962 | 12/1996 | Nicholas et al. | 604/52 |
| 5,597,804 | 1/1997 | Webb et al. | 514/18 |
| 5,605,892 | 2/1997 | Ikejiri et al. | 514/58 |
| 5,607,952 | 3/1997 | Badorc et al. | 514/326 |
| 5,612,369 | 3/1997 | Bone et al. | 514/423 |
| 5,612,378 | 3/1997 | Tianbao et al. | 514/602 |
| 5,626,562 | 5/1997 | Castro | 604/53 |
| 5,635,477 | 6/1997 | Degrado et al. | 514/11 |
| 5,637,599 | 6/1997 | Levy et al. | 514/326 |
| 5,679,690 | 10/1997 | Andre et al. | 514/314 |
| 5,713,853 | 2/1998 | Clark et al. | 604/53 |

OTHER PUBLICATIONS

Kerr, et al., Encoded Combinatorial Peptide Libraries Containing Non–Natural Amino Acids, J. Am. Chem. Soc. 115(6):2529–31 (1993).

Kluger, et al., Trimesoyltris(3,5–Dibromosalicylate): Specificity of Reactions of a Trifunctional Acylating Agent with Hemolobin, J. Am. Chem. Soc. 114:9275–79 (1992).

Krantz, Red Cell–Mediated Therapy: Opportunities and Challenges, Blood Cells, Molecules, and Diseases 23(3):58–68 (1997).

Kumada, et al., Comparative Study on Heparin and a Synthetic Thrombin Inhibitor No. 805 (MD–805*) in Experimental Antithrombin III–Deficient Animals, Thrombosis Research 24(4):285–98 (1981).

Kumon, et al., Anticoagulation with a Synthetic Thrombin Inhibitor After Cardiovascular Surgery and for Treatment of Disseminated Intravascular Coagulation, Critical Care Medicine 12(12):1039–43, 1104 (1984).

Magnani, et al., Preparation and Characterization of Biotinylated Red Blood Cells, Biotechnol. Appl. Biochem. 20:335–45 (1994).

Okamoto, et al., Potent Inhibition of Thrombin by the Newly Synthesized Arginine Derivative No. 805. The Importance of Stereostructure of its Hydrophobic Carboxamide Portion, Biochem. and Biophys. Res. Comm. 101(2):440–46 (1981).

Ota, et al., Clinical Evaluation of a New Thrombin Inhibitor Available for Haemodialysis, Proc. EDTA 20:144–49 (1983).

Rawson, et al., Separation of 21–(R)– and 21–(S)–Argatroban: Solubility and Activity of the Individual Diastereoisomers, J. Pharm. Sci. 82(6):672–73 (1983).

Sorensen, et al., Identification of the Interleukin–3 Receptor Using an Iodinatable, Cleavable, Photoreative Cross–Linking Agent, J. Biol. Chem. 261(20):9094–97 (1986).

Suzuki, et al., Biotinylated Erythrocytes: In Vivo Survival and In Vitro Recovery, Blood 70(3):791–95 (1987).

Taylor, et al., in Vivo Binding and Clearance of Circulating Antigen by Bispecific Heteropolymer–Mediated Binding to Primate Erythrocyte Complement Receptor, J. Immunol. 148(8): 2462–68 (1992).

Taylor, et al., Use of Heteropolymeric Monoclonal Antibodies to Attach Antigens to the C3b Receptor of Human Erythrocytes: a Potential Therapeutic Treatment, Proc. Natl. Acad. Sci. USA, 88:3305–09 (1991).

Titus, et al., Humna K/Natural Killer Cells Targeted with Hetero–Cross–Linked Antibodies Specifically Lyse Tumor Cells In Vitro and Prevent Tumor Growth In Vivo, J. Immunol. 139(9):3153–58 (1987).

Wakai, et al., Studies on Antigenicity of Argipidine (MD–805), Jpn. Pharmacol. Ther. 14:197–206, Supp. 5 (1986).

Wilson, et al., Rapid Whole Blood Assay for HIV–1 Seropositivity Using an Fab–Peptide Conjugate, J. Immunol. Methods 138(1):111–19 (1991) (Abstract).

Yokoyama, et al., Deferoxamine, a Promising Bifunctional Chelating Agent for Labeling Proteins with Gallium: Ga–67 DF–HSA: Concise Communication, J. Nucl. Med. 23:909–14 (1982).

Chemical Abstracts 128:29, abstract of Takahashi, 1995.

Chemical Abstracts 125:321384, Jones, 1995.

Chemical Abstracts 124:332313, Matsuzaki, 1995.

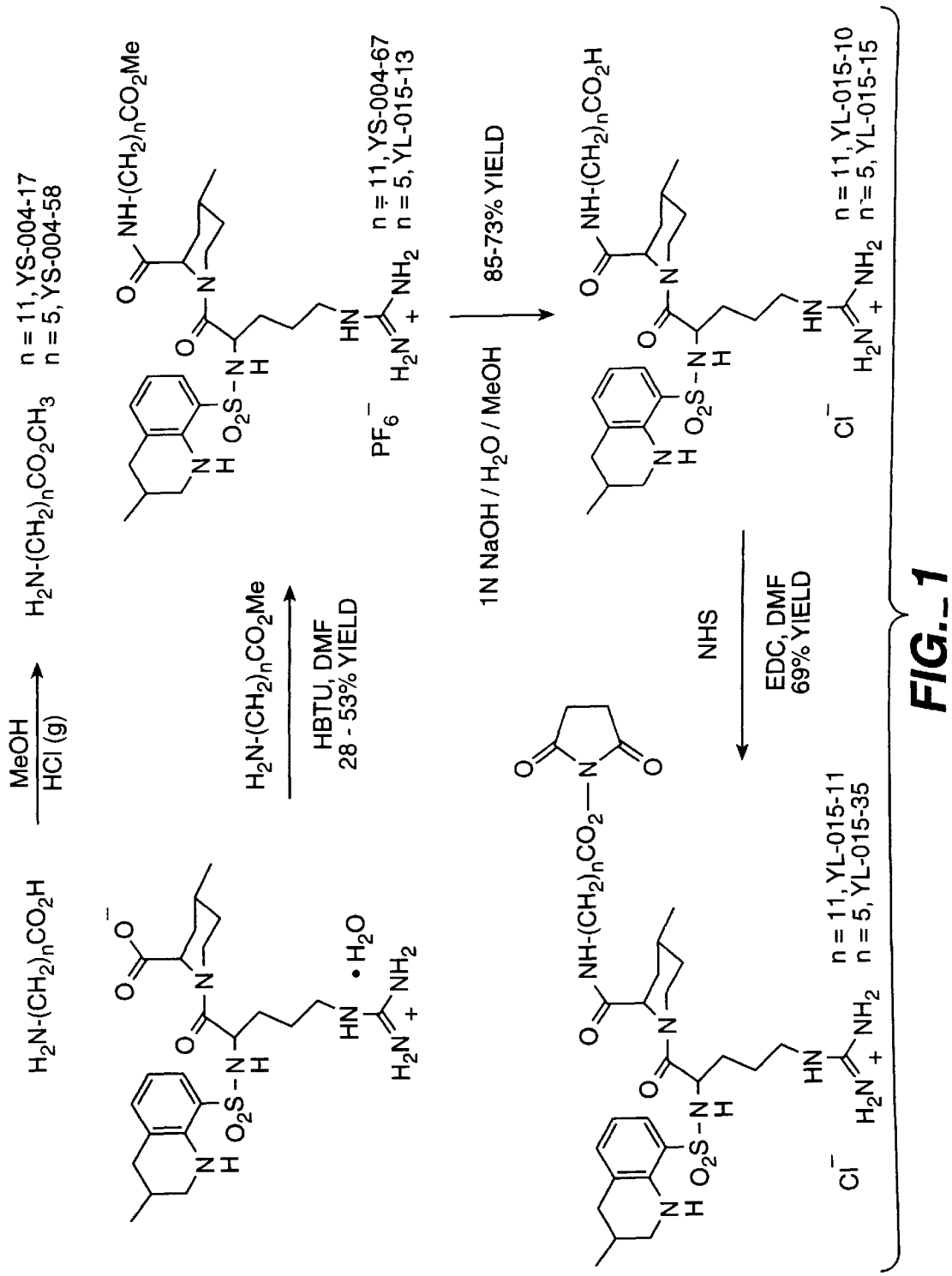
FIG._1

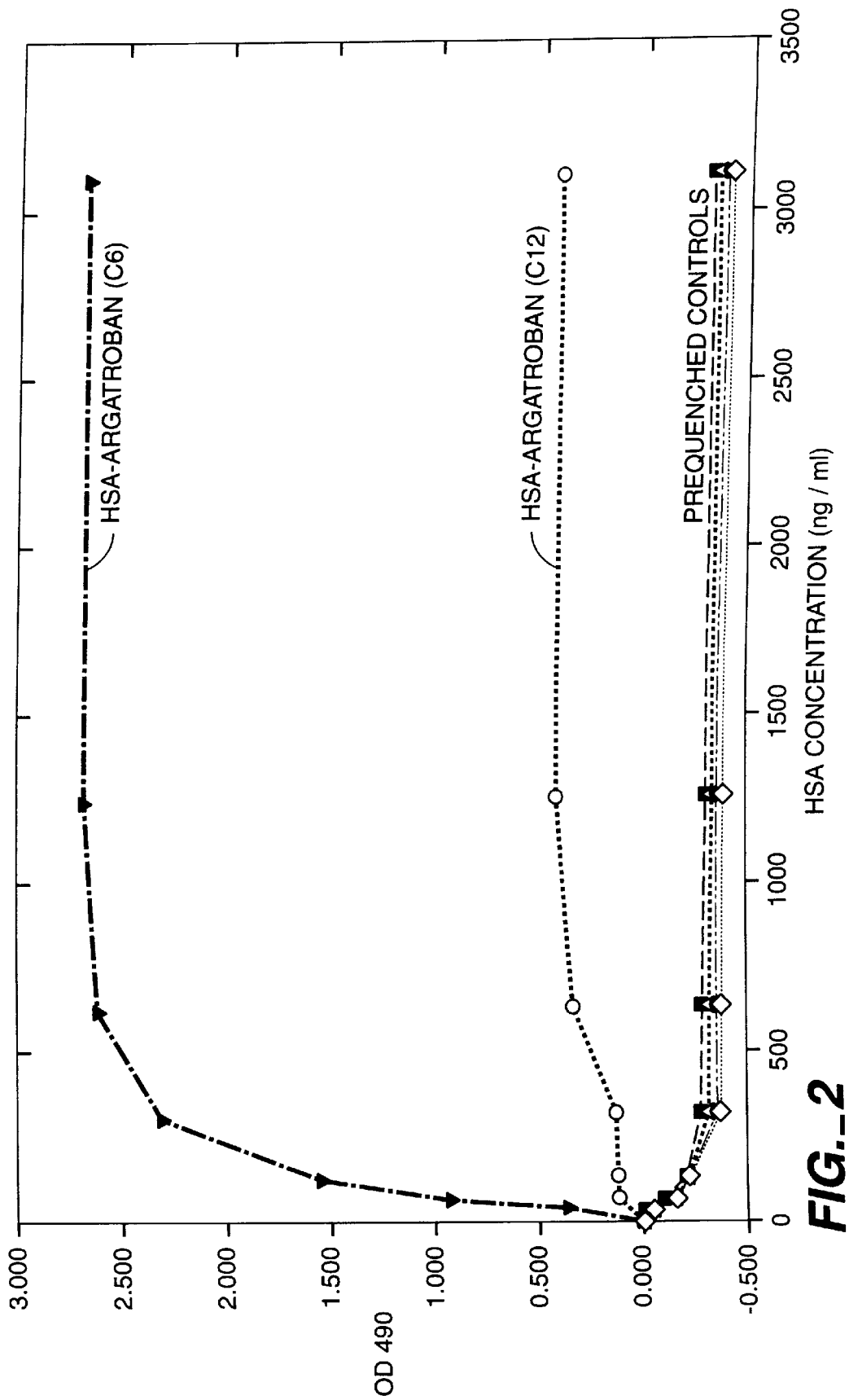
FIG._2

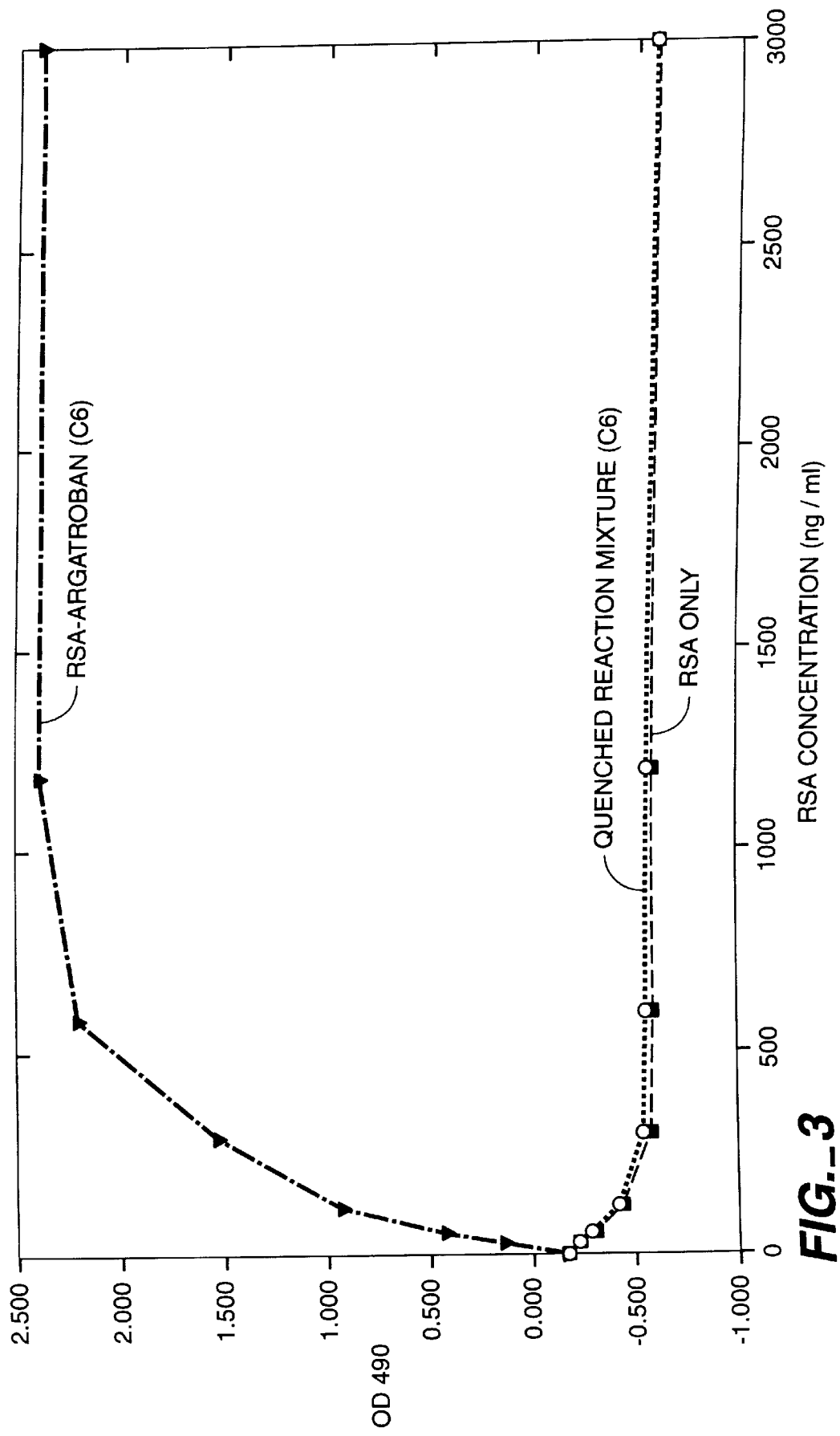
FIG._3

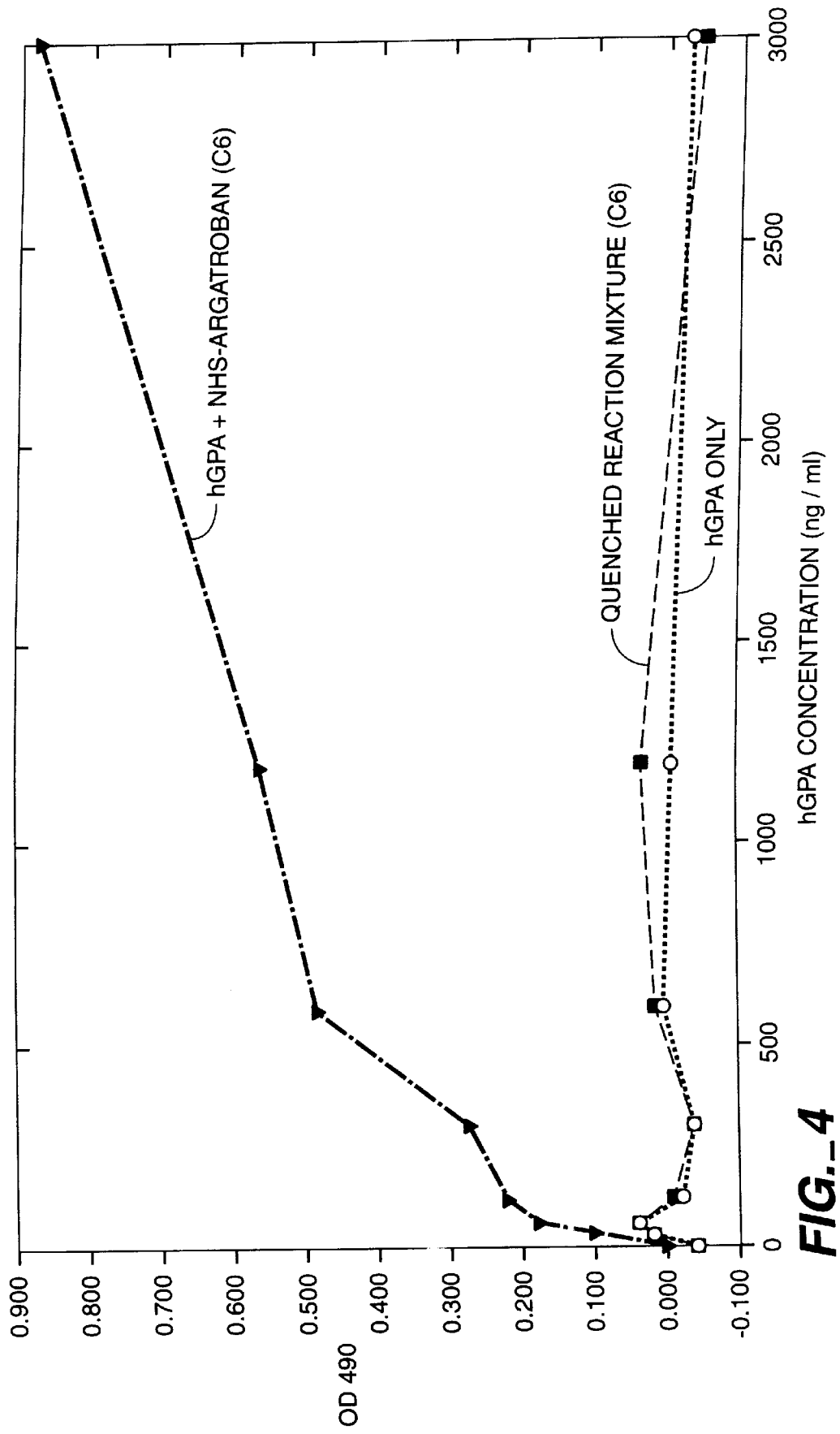
FIG._4

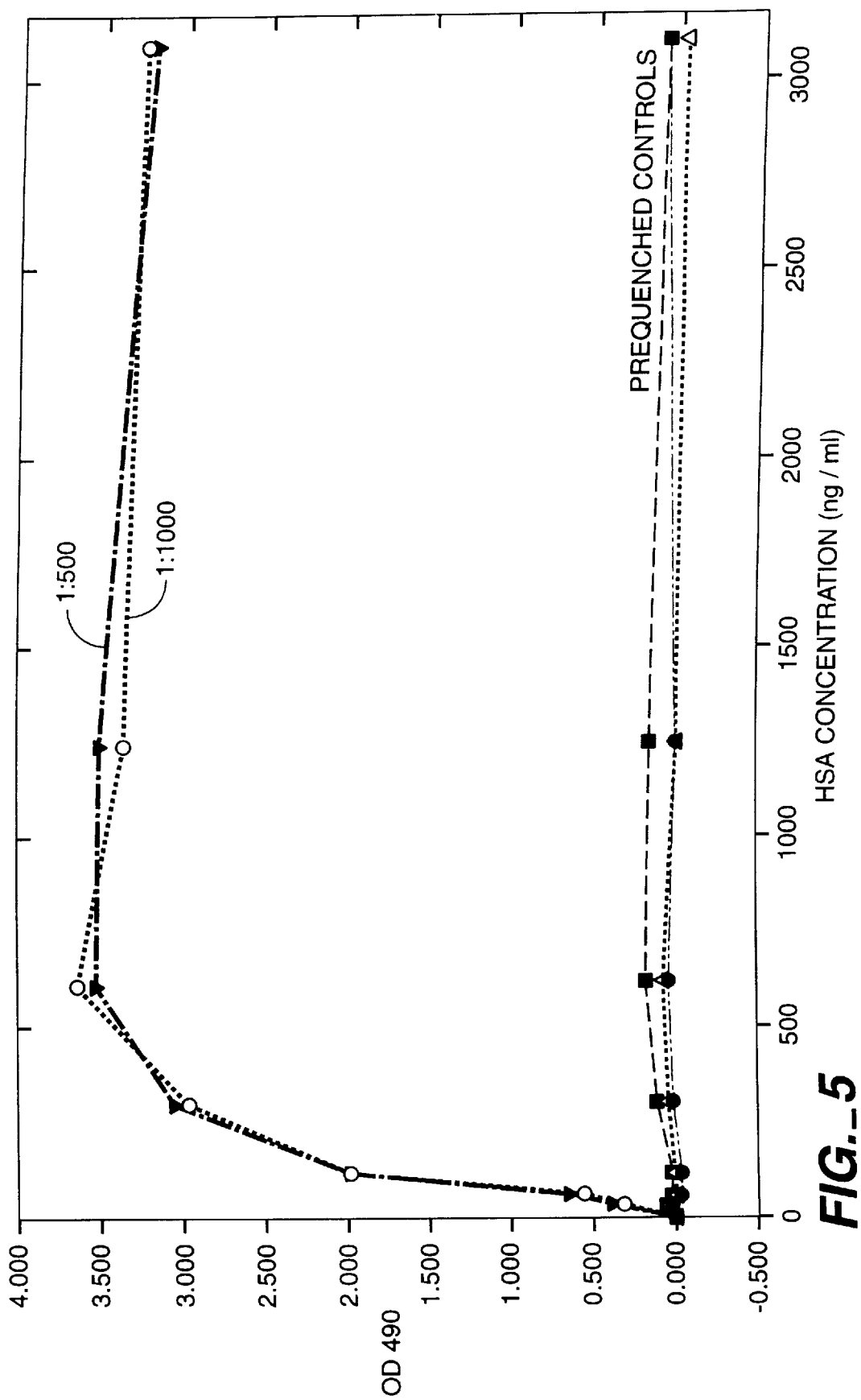
FIG._5

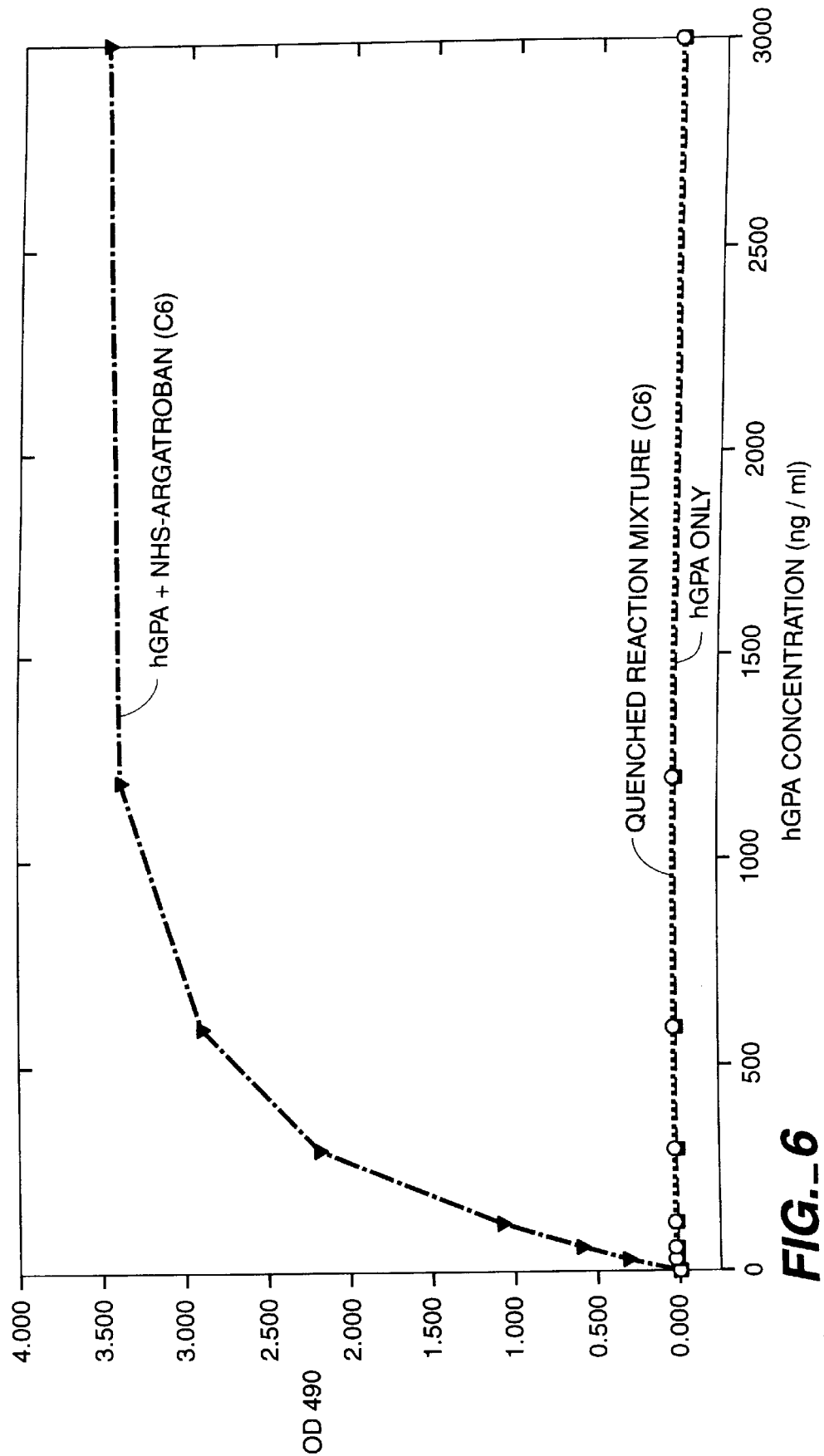
FIG._6

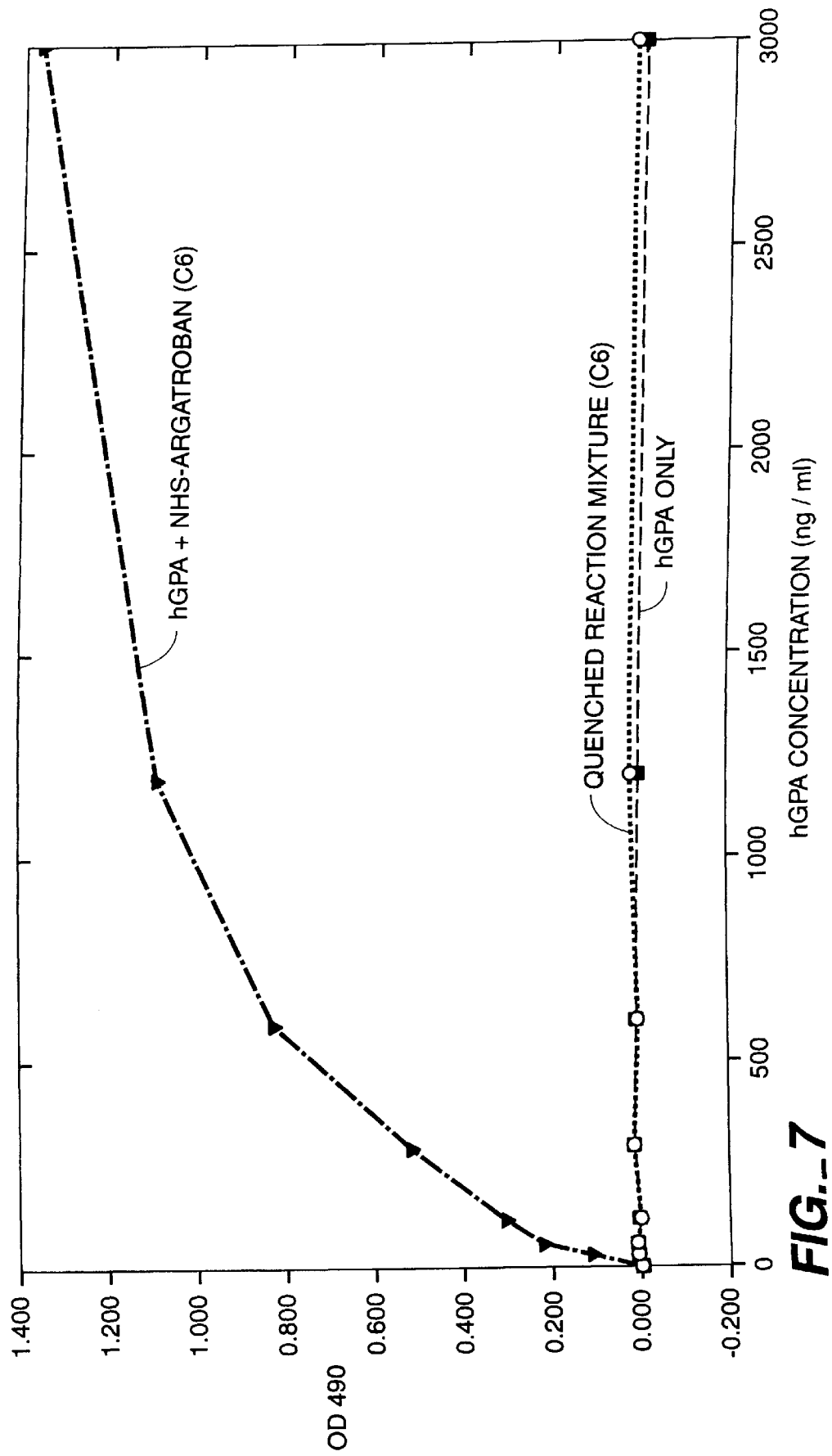
FIG._7

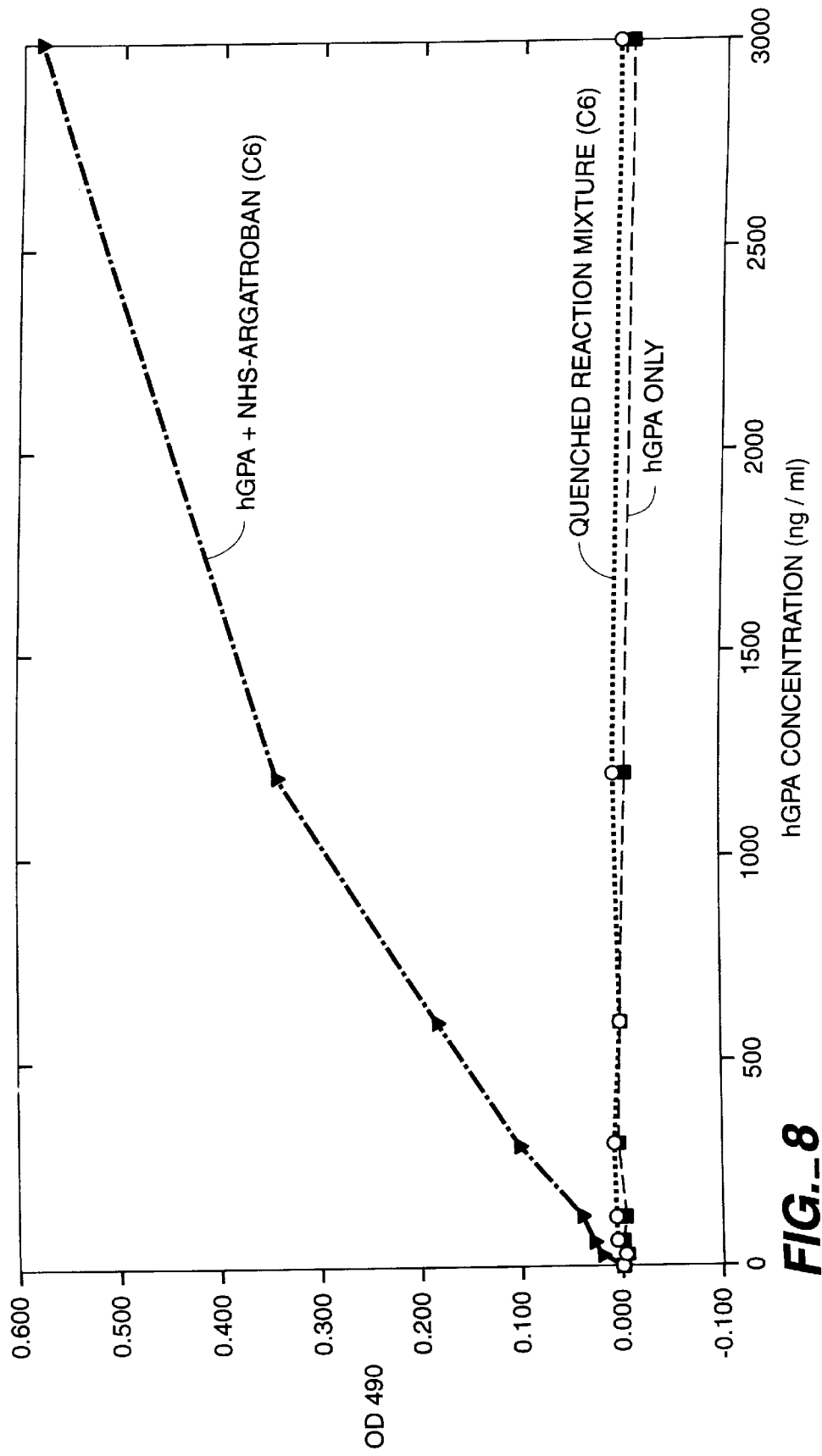
FIG._8

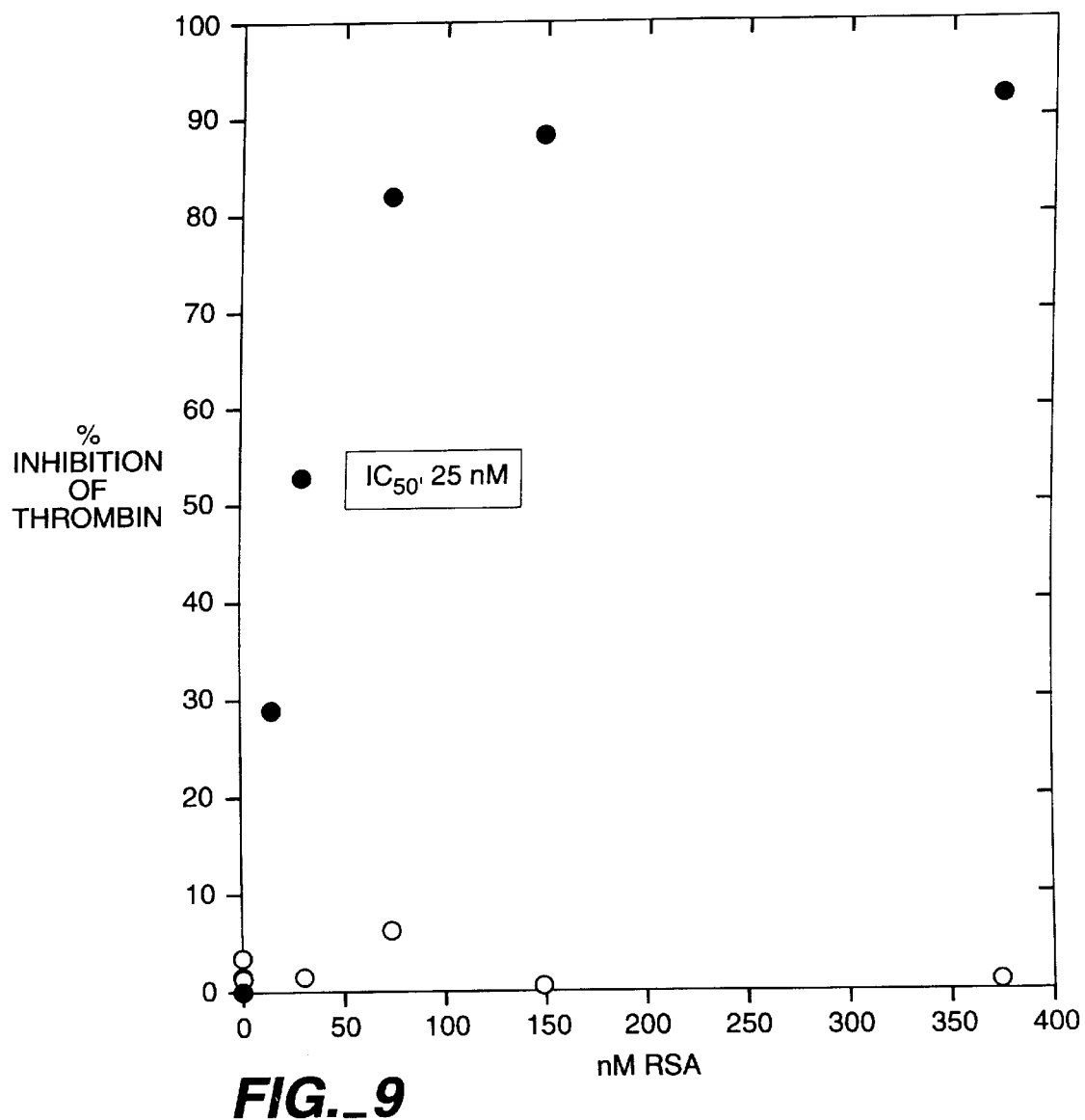
FIG._9

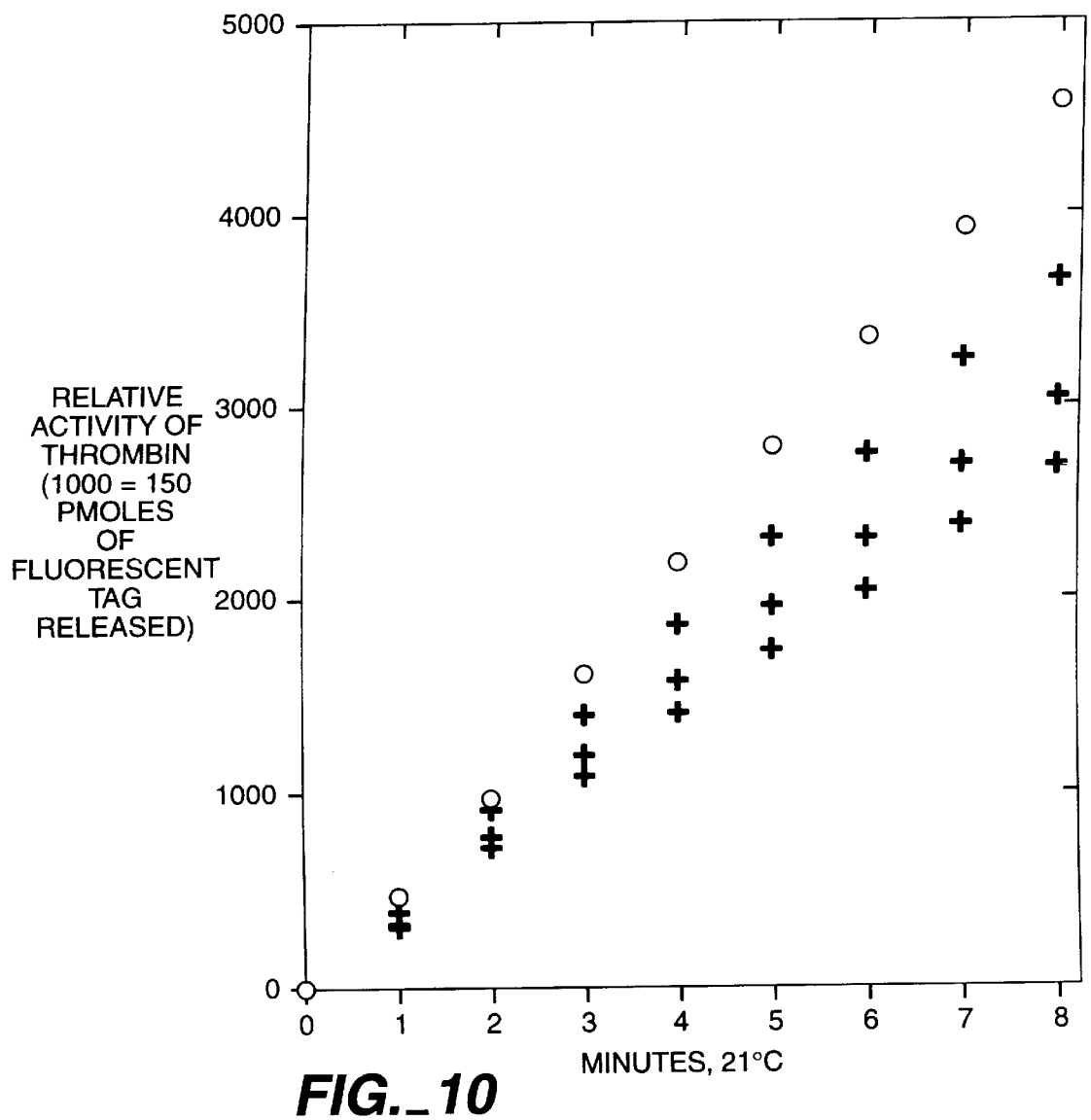
FIG._10

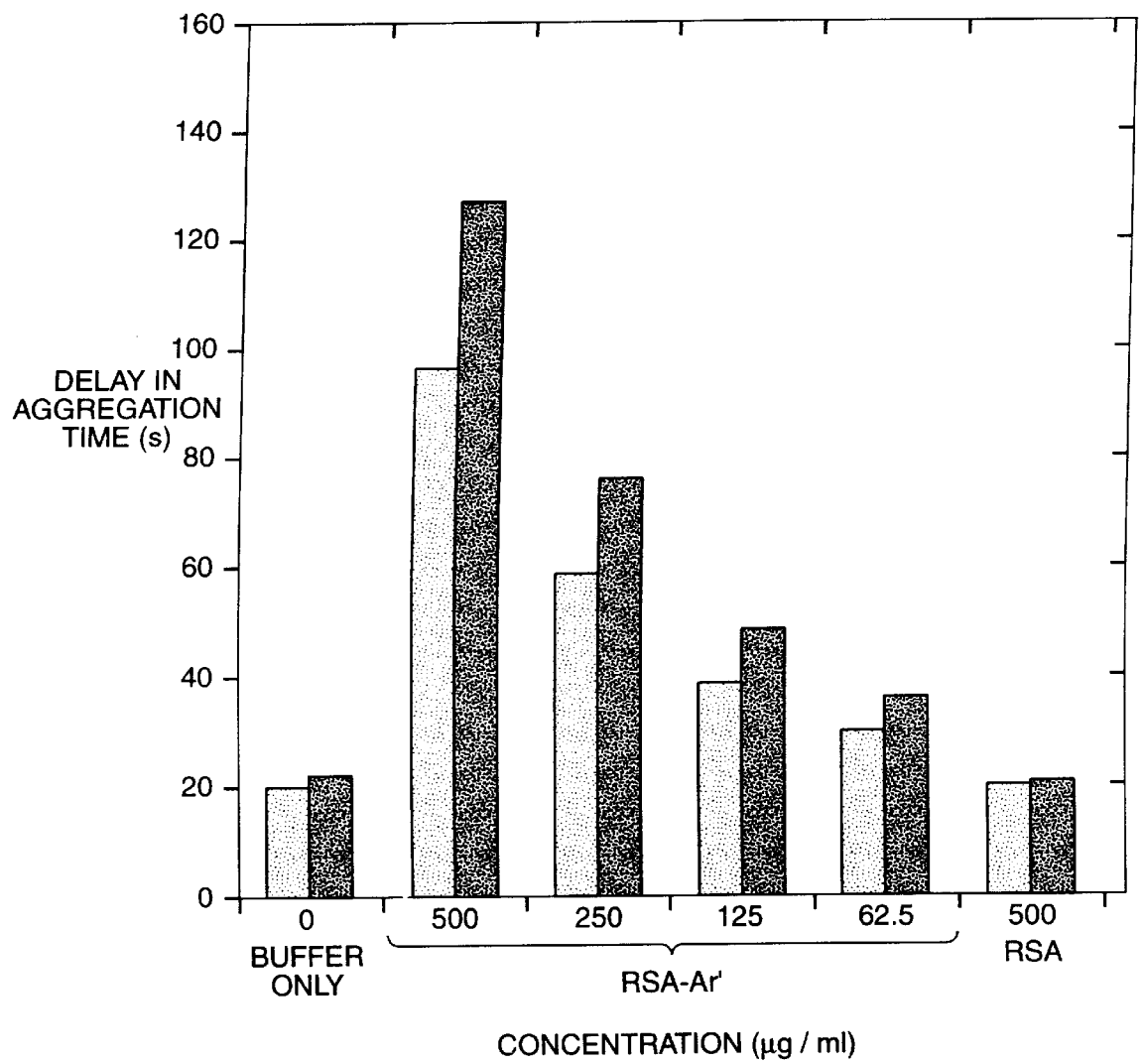
FIG._11

METHODS OF TREATING OR PREVENTING THROMBOSES

This application is a continuation application of U.S. patent application Ser. No. 09/108,534 filed Jul. 1, 1998 now U.S. Pat. No. 5,942,620 which is a continuation application of U.S. patent application Ser. No. 08/674,315 filed Jul. 1, 1996, now issued as U.S. Pat. No. 5,840,733.

TECHNICAL FIELD

The field of this invention is the extended lifetime of physiologically active agents in a mammalian host, more specifically, the extended lifetime of inhibitors of thrombin activity in a mammalian host.

BACKGROUND

In the past, there have been many attempts to obtain new and improved agents for the treatment of thrombosis. The $N^2$-(p-Tolysulfonyl)-L-arginine esters are one type of agent which can be used and these have been found to be effective in dissolving blood clots (see U.S. Pat. No. 3,622,615, issued Nov. 23, 1971). Another family of compounds which have been found to be particularly useful as highly specific inhibitors of thrombin for the control of thrombosis is the $N^2$-dansyl-L-arginine esters or amides (U.S. Pat. No. 3,978, 045) and many $N^2$-arylsulfonyl-L-argininamides. Moreover, another compound which has proven to be particularly useful for the treatment of thrombosis in mammals is 1-[5-[Aminoiminomethyl)amino]-1-oxo-2-[[(1,2,3,4-tetrahydro-3-methyl-8-quinolinyl)sulfonyl]-amino]pentyl]-4-methyl-2-piperidinecarboxylic acid, a compound which is commonly known as argatroban.

Although the above described compounds have proven useful for the treatment of disorders associated with abnormal thrombosis via inhibition of thrombin activity in vivo, their therapeutic utility is somewhat limited due to the fact that many of these compounds are quickly degraded and/or removed from the host's vascular system after administration. As such, for continuous thrombin inhibitory activity over extended periods of time, the above described thrombin inhibitors must be administered as a large bolus given at periodic time intervals or by providing depots comprising the drug. Unfortunately, however, administration of large boluses at periodic time intervals often results in subtherapeutic doses of the drug for extended periods of time followed by doses which may greatly exceed the desired therapeutic level. The latter may often involve serious adverse side effects. Moreover, although various pumps and biodegradable and non-biodegradable capsules have been devised for the delivery of drug over an extended period of time, these devices may have a variety of shortcomings in their profile of drug delivery, for example, often resulting in an inflammatory response and/or being subject to interference in their release of active drug.

There is, therefore, an interest in providing improved therapies associated with thrombin inhibition.

SUMMARY OF THE INVENTION

Novel compounds are provided comprising chemically reactive intermediates which can react with available reactive functionalities on blood components to form covalent linkages, where the resulting covalently-bound conjugates are found to have thrombin inhibition activity. Specifically, the compounds of the present invention are chemically reactive derivatives of the known thrombin inhibitor 1-[5-[Aminoiminomethyl)amino]-1-oxo-2-[[(1,2,3,4-tetrahydro-3-methyl-8-quinolinyl)sulfonyl]-amino]pentyl]-4-methyl-2-piperidinecarboxylic acid, a compound also known as argatroban. The derivatized argatroban molecules of the present invention comprise an active thrombin inhibitor portion and become covalently linked through a chemically reactive group to reactive functionalities on various blood components. The conjugated thrombin inhibitor molecules thereby have extended lifetimes in the bloodstream, as compared to the unconjugated parent drug, and are, therefore, capable of maintaining thrombin inhibitory activity for extended periods of time as compared to the unconjugated parent drug.

Also provided herein are compositions comprising the derivatized thrombin inhibitor molecules described above combined with pharmaceutically acceptable carriers and methods for inhibiting thrombin activity in vivo comprising administering to the bloodstream of a mammalian host the novel compounds of the present invention.

BRIEF DESCRIPTION OF THE DRAWINGS

FIG. 1 is a schematic depiction of the steps involved in the synthesis of various derivatized thrombin inhibitor molecules of the present invention.

FIG. 2 is a graph showing the results obtained in sandwich ELISA assays with human serum albumin (HSA) alone ("●"), HSA treated with prequenched hydroxylamine treated argatroban-C6 NHS ester ("Δ"), HSA treated with prequenched argatroban-C12 NHS ester ("*"), HSA reacted with argatroban-C6 NHS ester ("◆") or HSA reacted with argatroban-C12 NHS ester ("X"). Results are presented as the absorbance at 490 nm ("OD 490") versus HSA concentration in nanograms per milliliter ("ng/ml").

FIG. 3 is a graph showing the results obtained in sandwich ELISA assays with rabbit serum albumin (RSA) alone ("Δ"), RSA reacted with prequenched argatroban-C6 NHS ester ("■") or RSA reacted with argatroban-C6 NHS ester ("◆"). Results are presented as the absorbance at 490 nm ("OD 490") versus RSA concentration in nanograms per milliliter ("ng/ml").

FIG. 4 is a graph showing the results obtained in sandwich ELISA assays with human glycophorin A (hGPA) alone ("Δ"), hGPA treated with prequenched argatroban-C6 NHS ester ("■") or hGPA treated with argatroban-C6 NHS ester ("◆"). Results are presented as the absorbance at 490 nm ("OD 490") versus hGPA concentration in nanograms per milliliter ("ng/ml").

FIG. 5 is a graph showing the results obtained in sandwich ELISA assays with HSA alone ("■"), HSA treated with prequenched argatroban-C6 NHS ester ("*"), HSA treated with argatroban-C6 NHS ester (1:500 dilution) ("◆") or HSA reacted with argatroban-C6 NHS ester (1:1000 dilution) ("X"). Results are presented as the absorbance at 490 nm ("OD 490") versus HSA concentration in nanograms per milliliter ("ng/ml").

FIG. 6 is a graph showing the results obtained in sandwich ELISA assays with hGPA alone ("Δ"), hGPA treated with prequenched argatroban-C6 NHS ester ("■") or hGPA reacted with argatroban-C6 NHS ester ("◆") employing the 5F4 monoclonal antibody. Results are presented as the absorbance at 490 nm ("OD 490") versus hGPA concentration in nanograms per milliliter ("ng/ml").

FIG. 7 is a graph showing the results obtained in sandwich ELISA assays with hGPA alone ("Δ"), hGPA treated with prequenched argatroban-C6 NHS ester ("■") or hGPA reacted with argatroban-C6 NHS ester ("◆") employing the 3C10 monoclonal antibody. Results are presented as the absorbance at 490 nm ("OD 490") versus hGPA concentration in nanograms per milliliter ("ng/ml").

FIG. 8 is a graph showing the results obtained in sandwich ELISA assays with hGPA alone ("Δ"), hGPA treated with prequenched argatroban-C6 NHS ester ("■") or hGPA reacted with argatroban-C6 NHS ester ("♦") employing the 3E4 monoclonal antibody. Results are presented as the absorbance at 490 nm ("OD 490") versus hGPA concentration in nanograms per milliliter ("ng/ml").

FIG. 9 is a graph showing the results obtained in thrombin inhibitor assays with RSA alone ("○") or RSA reacted with argatroban-C6 NHS ester ("●"). Results are presented as the % inhibition of thrombin versus the amount of RSA employed in nM.

FIG. 10 is a graph showing the results obtained in thrombin inhibitor assays with thrombin alone ("○") or erythrocyte ghosts reacted with argatroban-C6 NHS ester ("+"). The points on the graph wherein conjugated erythrocyte ghosts were employed are each shown by the symbol ("+") however, those points define 3 parallel lines representing (from the top of the graph to the bottom) the addition of 200 µg, 450 µg and 600 µg of ghosts/ml. Results are presented as the thrombin activity versus the number of minutes at 21° C.

FIG. 11 is a graph showing the results obtained demonstrating the ability of the novel thrombin inhibitors of the present invention, when covalently bound to RSA, to delay thrombin-induced platelet aggregation. Data is presented as the concentration in µg/ml of RSA alone ("RSA") or RSA covalently bound by argatroban-C6 NHS-ester molecules ("RSA-Ar") versus the time in minutes to acheive 50% platelet aggregation. Assays were run in duplicate and each assay is shown as a separate column at each concentration tested.

DETAILED DESCRIPTION OF THE INVENTION

Methods and compositions are provided for the treatment of patients having disorders associated with abnormal thrombosis through inhibition of the mammalian protein, thrombin. The method employs a novel thrombin inhibitor compound comprising a derivative of the known thrombin inhibitor argatroban, wherein the novel thrombin inhibitor compound has a chemically reactive group which reacts with available reactive functionalities on various blood components, thereby covalently bonding the derivatized thrombin inhibitor molecule to those blood components. The chemically reactive group is at a site, so that when the thrombin inhibitor portion is bonded to the blood component, the thrombin inhibitor portion retains a substantial proportion of the parent compound's inhibitory activity. Therefore, through the covalent bonding of the subject thrombin inhibitor molecules to long-lived blood components, the effective lifetime of the thrombin inhibitor in the host's vascular system is greatly increased.

The various sites with which the chemically reactive group of the subject thrombin inhibitor molecules may react include cells, particularly red blood cells (erythrocytes) and platelets, and proteins, such as immunoglobulins, including IgG and IgM, serum albumin, ferritin, steroid binding proteins, transferrin, thyroxin binding protein, α-2-macroglobulin, and the like. Those proteins with which the derivatized thrombin inhibitor compounds react, which are not long-lived, will generally be eliminated from the host within about three days, so that the proteins indicated above (including the proteins of the cells) will remain at least three days, usually at least four days, and may remain five days or more, usually not exceeding 60 days, more usually not exceeding 30 days, particularly as to the half life, based on the concentration in the blood, as measured in from about 1–3 hours after administration.

For the most part, reaction will be with mobile components in the blood, particularly blood proteins and cells, more particularly blood proteins and erythrocytes. By "mobile" is intended that the component does not have a fixed situs for any extended period of time, generally not exceeding 5, more usually one minute, although some of the blood component may be relatively stationary for extended periods of time. Initially, there will be a relatively heterogeneous population of functionalized proteins and cells. However, for the most part, the population within a few days will vary substantially from the initial population, depending upon the half-life of the functionalized proteins in the blood stream. Therefore, usually within about three days or more, IgG will become the predominant functionalized protein in the blood stream.

Usually, by day 5 post-administration, IgG, serum albumin and erythrocytes will be at least about 60 mole %, usually at least about 75 mole %, of the conjugated components in blood, with IgG, IgM (to a substantially lesser extent) and serum albumin being at least about 50 mole %, usually at least about 75 mole %, more usually at least about 80 mole %, of the noncellular conjugated components.

The derivatized thrombin inhibitor molecules of the present invention will, for the most part, have the following formula:

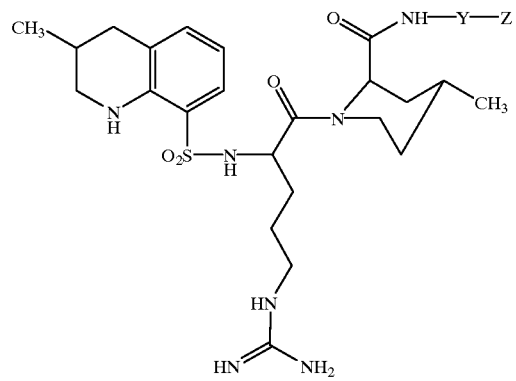

wherein:

Y is a linking group having from 2–30, more usually from 2–18, preferably from 6–12 atoms in the chain, particularly carbon, oxygen, phosphorous and nitrogen, more particularly carbon and oxygen, where Y may be alkylene, oxyalkylene, or polyoxyalkylene, preferably an alkyl chain having from 2–15, more preferably from 6–12 carbon atoms in the alkyl chain, and the like; and Z is a chemically reactive group or precursor to a chemically reactive group, such as carboxy, carboxy ester, where the ester group is of 1–8, more usually 1–6 carbon atoms, particularly a physiologically acceptable leaving group which activates the carboxy carbonyl for reaction with amino groups in an aqueous system, e.g. N-hydroxysuccininide, isocyanate, thiolester, thionocarboxylic acid ester, imino ester, mixed anhydride, e.g. carbodiimide anhydride, carbonate ester, phosphoryl ester, etc. and the like.

The activatable precursor will usually be a non-oxocarbonyl group, including the sulfur and nitrogen analogs thereof, such as thiono and thiol acids and esters and imino esters or functionalities which can be directly modified to provide an active functionality, e.g. cyano.

The reactive functionalities which are available on proteins for covalently bonding to the chemically reactive group of the derivatized thrombin inhibitors of the present invention are primarily amino groups, carboxyl groups and thiol groups. While any of these may be used as the target of the chemically reactive group on the thrombin inhibitor, for the most part, bonds to amino groups will be employed, particularly with the formation of amide bonds. To form amide bonds, one may use as a chemically reactive group a wide-variety of active carboxyl groups, particularly esters, where the hydroxyl moiety is physiologically acceptable at the levels required. While a number of different hydroxyl groups may be employed, the most convenient will be N-hydroxysuccinimide (NHS), and N-hydroxy sulfosuccinimide (sulfo-NHS), although other alcohols, which are functional in an aqueous medium such as blood, may also be employed. In some cases, special reagents find use, such as azido, diazo, carbodiimide anhydride, hydrazine, dialdehydes, thiol groups, or amines to form amides, esters, imines, thioethers, disulfides, substituted amines, or the like. Usually, the covalent bond which is formed should be able to be maintained during the lifetime of the blood component, unless it is intended to be a release site.

If desired, the subject conjugates may also be prepared in vitro by combining blood with derivatized thrombin inhibitors of the present invention, allowing covalent bonding of the derivatized thrombin inhibitors to reactive functionalities on blood components and then returning the conjugated blood to the host. Moreover, the above may also be accomplished by first purifying an individual blood component or limited number of components, such as red blood cells, immunoglobulins, serum albumin, or the like, and combining the component or components in vitro with the chemically reactive thrombin inhibitors. The functionalized blood or blood component may then be returned to the host to provide in vivo the subject therapeutically effective conjugates. The blood also may be treated to prevent coagulation during handling in vitro.

When conjugates are prepared in vitro, the ratio of derivatized thrombin inhibitor to blood components will vary widely, depending upon whether whole compound intravascularly. Included are red blood cells (half life ca. 60 days), platelets (half life ca. 4–7 days), endothelial cells lining the blood vasculature, and long lived blood serum proteins, such as albumin, steroid binding proteins, ferritin, $\alpha$-2-macroglobulin, transferrin, thyroxin binding protein, immunoglobulins, especially IgG, etc. In addition to preferred half lives, the subject components are preferably in cell count or concentration sufficient to allow binding of therapeutically useful amounts of the compound of the present invention. For cellular long lived blood components, cell counts of at least 2,000/$\mu$l and serum protein concentrations of at least 1 $\mu$g/ml, usually at least about 0.01 mg/ml, more usually at least about 1 mg/ml, are preferred.

The cellular long lived blood components to which the subject derivatized thrombin inhibitors bond are present in high number in the vascular system. Platelets are present in from about 1–4×10$^5$/$\mu$l, while red blood cells are present in about 4–6×10$^6$/$\mu$l. The cells have a long half life and the binding to a surface membrane protein of the cells appears not to result in endocytosis. Preferred cells have a wide distribution in capillaries and tissue and express specific binding sites on the cell surface associated with their specific differentiation. In addition to in vivo administration of the subject derivatized thrombin inhibitors, in the case of red blood cells and platelets, these cells may be readily collected, combined with the conjugate in vitro, and then administered to the host. The cells will normally be autologous or allogeneic, but in some instances may even be xenogeneic.

Suitable erythrocyte binding site containing molecules include glycophorin A, B and C, Band 3 and Rhesus blood group antigens. Preferred erythrocyte binding sites are abundantly expressed on the erythrocyte with copy numbers of at least 1,000, preferably at least 10,000, more preferably at least 100,000 per cell, desirably are tethered at least about 0.5, preferably at least about 1 nm above the bilayer surface and do not facilitate per se cell deformation when the derivatized thrombin inhibitor molecule is bound to the cell (e.g. the binding will be selected so as not to be a key component of the cytoskeleton). Binding sites of the erythrocyte surface glycoprotein glycophorin A and erythrocyte binding sites comprising sialic blood or just a purified component is used as a bonding site for the derivatized thrombin inhibitor. For reacting with whole blood, one will normally have a ratio of derivatized thrombin inhibitor to blood of about 38 micrograms per ml to about 300 micrograms per ml, respectively, while the ratio of derivatized thrombin inhibitor to 10$^9$ cells will be in the range of about 7.6 micrograms to about 300 micrograms, while the ratio of derivatized thrombin inhibitor to 1 mg of protein will be in the range of about 38 micrograms to about 300 micrograms.

The nature of the thrombin inhibitor compound may provide for random bonding to the long lived blood components or, to varying degrees, targeted bonding to a restricted class of blood components. For random bonding, the distribution of the thrombin inhibitor compound will be based on the relative proportion of active sites for bonding of the blood components, the mode of administration and whatever preferential association the thrombin inhibitor may have. For targeted bonding, a part of the thrombin inhibitor compound will be a group which preferentially noncovalently binds to one or more sites present on one or more of the blood components. For this purpose, entities which are known to complex with particular blood components may be used. Alternatively, one may prepare a combinatorial library and screen for members of the library which provide the desired blood component association spectrum. For the most part, random bonding will be employed.

To the extent that targeted bonding is employed, the choice of the long lived blood component will be affected, at least in part, by the desired lifetime for the drug and the availability of the blood component for bonding to the derivatized thrombin inhibitor.

A long lived blood component has a half life of at least about 12 hours, usually at least about 48 hours, preferably at least about 5 days, desirably at least about 10 days and more desirably at least about 20 days or more. Generally, half lives are determined by serial measurements of whole blood, plasma or serum levels of the compound following labeling of the compound with an isotope (e.g. $^{131}$I, $^{125}$I, Tc, $^{51}$Cr $^3$H, etc.) or fluorochrome and injection of a known quantity of labeled acid are examples of preferred binding sites. Preferred platelet binding sites include GPIIa, GPIIb, GPIIIa and GPIV. Desirably, upon bonding to the target, deformation of the long-lived blood component, e.g. erythrocyte or platelet, does not occur.

The derivatized thrombin inhibitors of the present invention will usually be administered as a bolus, but may be introduced slowly over time by infusion using metered flow, or the like. Alternatively, although less preferable, blood may be removed from the host, treated ex vivo, and returned to the host. The derivatized thrombin inhibitors will be administered in a physiologically acceptable medium, e.g. deionized water, phosphate buffered saline (PBS), saline, aqueous ethanol or other alcohol, plasma, proteinaceous solutions, mannitol, aqueous glucose, alcohol, vegetable oil, or the like. Other additives which may be included include buffers, where the media are generally buffered at a pH in the range of about 5 to 10, where the buffer will generally range in concentration from about 50 to 250 mM, salt, where the concentration of salt will generally range from about 5 to 500 mM, physiologically acceptable stabilizers, and the like. The compositions may be lyophilized for convenient storage and transport.

The subject derivatized thrombin inhibitors will for the most part be administered parenterally, such as intravascularly (IV), intraarterially (IA), intramuscularly (IM), subcutaneously (SC), or the like. Administration may in appropriate situations be by transfusion. In some instances, where reaction of the active functional group is relatively slow, administration may be oral, nasal, rectal, transdermal or aerosol, where the nature of the conjugate allows for transfer to the vascular system. Usually a single injection will be employed although more than one injection may be used, if desired. The derivatized thrombin inhibitors may be administered by any convenient means, including syringe, trocar, catheter, or the like. The particular manner of administration will vary depending upon the amount to be administered, whether a single bolus or continuous administration, or the like. Preferably, the administration will be intravascularly, where the site of introduction is not critical to this invention, preferably at a site where there is rapid blood flow, e.g. intravenously, peripheral or central vein. Other routes may find use where the administration is coupled with slow release techniques or a protective matrix. The intent is that the subject compound be effectively distributed in the blood, so as to be able to react with the blood components. The concentration of the conjugate will vary widely, generally ranging from about 1 pg/ml to 50 mg/ml. The total administered intravascularly will generally be in the range of about 0.1 mg/ml to about 10 mg/ml, more usually about 1 mg/ml to about 5 mg/ml.

The manner of producing the derivatized thrombin inhibitors of the present invention will vary widely, depending upon the nature of the various elements comprising the molecule. The synthetic procedures will be selected so as to be simple, provide for high yields, and allow for a highly purified product. Normally, the chemically reactive group will be created as the last stage, for example, with a carboxyl group, esterification to form an active ester will be the last step of the synthesis. An illustrative method for the production of the derivatized thrombin inhibitors of the present invention is shown in FIG. 1.

By bonding to long-lived components of the blood, such as immunoglobulin, serum albumin, red blood cells and platelets, a number of advantages ensue. The inhibition of the thrombin protein is extended for days to weeks. Only one administration need be given during this period of time. Greater specificity can be achieved, since the active compound will be primarily bound to large molecules, where it is less likely to be taken up intracellularly to interfere with other physiological processes.

The blood of the mammalian host may be monitored for the presence of the thrombin inhibitor one or more times. By taking a portion or sample of the blood of the host, one may determine whether the thrombin inhibitor has become bound to the long lived blood components in sufficient amount to be therapeutically active and, thereafter, the level of thrombin inhibition activity in the blood. If desired, one may also determine to which of the blood components the thrombin inhibitor molecule is bound.

The derivatized thrombin inhibitors of the present invention will find use in a variety of different applications. For example, the novel thrombin inhibitors of the present invention are useful for the treatment and/or prevention of disorders associated with abnormal thrombosis. The subject thrombin inhibitor molecules are useful for inhibiting the production of thromboses, accelerating the dissolution of existing thromboses and for maintaining and/or improving blood circulation. The subject derivative molecules will also find use, for example, for treatment after surgery, after myocardial infarction, arteritis of the legs, deep venous thrombosis, pulmonary embolism, and the like.

The following examples are offered by way of illustration and not by way of limitation.

EXPERIMENTAL

EXAMPLE 1

Synthesis of Extended Lifetime Derivatized Thrombin Inhibitor Molecules

Materials and Methods: The synthesis of various derivatized extended lifetime thrombin inhibitor (argatroban-derived) molecules is schematically diagrammed in FIG. 1 and is described below.

(1) Synthesis of Methyl 12-Aminododecanoate (compound YS-004-17). To a suspension of 12-aminododecanoic acid (5.00 g, 23.3 mmol) in anhydrous MeOH (90 mL) was introduced hydrogen chloride gas for 25 minutes, during which time the suspension became clear. The solution was then stirred at room temperature for 3 hours and the solvent was removed in vacuo. The white solid residue was dissolved in $H_2O$. Solid $NaHCO_3$ was added to neutralize the solution to pH 8–9. The white precipitates thus formed were collected by vacuum filtration (5.20 g) (Yield: 98%).

$^1$HNMR (MeOH-d4, 300 MHz) δ 3.67 (s, 3H, $OCH_3$), 2.68 (t, 2H, J=7.1 Hz, $NCH_2$), 2.30 (t, 2H, J=7.5 Hz, $CH_2CO_2$), 1.68–1.56 (m, 2H, $CH_2$), 1.50–1.38 (m, 2H, $CH_2$), 1.27 (br. s, 12 H, $(CH_2)_6$), 1.20–0.90 (m, 2H, $CH_2$).

(2) Synthesis of Methyl 6-Aminohexanoate (compound YS-004-58). To a suspension of 6-aminocaproic acid (3.00 g, 22.9 mmol) in anhydrous MeOH (60 nL) was introduced hydrogen chloride gas for 25 minutes, during which time the suspension became clear. The solution was then stirred at room temperature for 5 hours and MeOH was removed in vacuo. The residue was recrystallized from THF to give a white solid (3.10 g). (Yield: 75%).

$^1$HNMR (MeOH-d4, 300 MHz) δ 3.66 (s, 3H, $OCH_3$), 2.92 (t, 2H, J=7.7 Hz, $NCH_2$), 2.37 (t, 2H, J=7.2 Hz, $CH_2 CO_2$), 1.74–1.60 (m, 4H, $CH_2CH_2$), 1.48 –1.36 (m, 2H, $CH_2$)

3. Synthesis of Argatroban-C12 Methyl Ester (compound YS-004-67). To a solution of argatroban monohydrate (300 mg, 0.570 mmol) and methyl 12-aminododecanoate (compound YS-004-17) (132 mg, 0.576 mmol) in anhydrous DMF (15 mL) was added HBTU (258 mg, 0.680 mmol). Stirring was continued at room temperature for 16 hours. The precipitates formed during the reaction were filtered off and DMF was removed by vacuum distillation. The residue was purified by preparative TLC using solvents $CH_2Cl_2$/MeOH/$NH_3$ (90/10/1, v/v) to give the titled compound (140 mg) (Yield: 28%). $^1$HNMR (MeOH-d4, 300 MHz).

4. Synthesis of Argatroban-C6 Methyl Ester (compound YL-015-13). To a solution of argatroban monohydrate (100 mg, 0.190 mmol) and methyl 6-aminohexanoate hydrochloride (compound YS-004-58) (35 mg, 0.193 mmol) in anhydrous DMF (5 mL) was added triethylamine (23 mg, 0.23 mmol), followed by addition of HBTU (86 mg, 0.23 mmol). Stirring was continued at room temperature for 20 hours. The precipitates formed during the reaction were filtered off and DMF was removed by vacuum distillation. The residue was purified by preparative TLC using solvents $CH_2Cl_2$/MeOH/$NH_3$ (90/10/1, v/v) to give the titled compound (78 mg) (Yield: 53%). $^1$HNMR (MeOH-d4, 300 MHz).

5. Synthesis of Argatroban-C12 Free Acid (compound YL015-10). A solution of compound YS-004-67 (225 mg, 0.260 mmol) in MeOH (4.2 mL) and 1 M aqueous NaOH (0.87 mL) was stirred at room temperature for 24 hours. MeOH was removed in vacuo to give a cloudy solution, to which more $H_2O$ was added until the solution became clear. The solution was acidified with 1 N HCl to pH 3.0 while being cooled at 0° C. to give a white precipitate, which was collected by vacuum filtration to afford the titled compound (105 mg). The filtrate was extracted with n-butanol (4×4 mL). The combined butanol solution was washed with $H_2O$ (to pH 5.0) and concentrated in vacuo azeotropically with $H_2O$ to give another portion of the compound (58 mg) (Yield: 85%). $^1$HNMR (MeOH-d4, 300 MHz).

6. Synthesis of Argatroban-C6 Free Acid (compound YL-015-15). A solution of compound YL-015-13 (124 mg, 0.159 mmol) in MeOH (3 mL) and 1 M aqueous NaOH (0.55 mL) was stirred at room temperature for 33 hours. The reaction was worked up by the same procedure as described for the preparation of compound YL-015-10, to give the titled compound (76 mg) (Yield: 73%). $^1$HNMR (MeOH-d4, 300 MHz).

7. Synthesis of Argatroban-C12 NHS Ester (compound YL-015-11). To a solution of compound YL-015-10 (40 mg, 0.054 mmol) and N-hydroxysuccinimide (13 mg, 0.11 mmol) was added diisopropylethylamine (7.4 mg, 0.057 mmol), followed by addition of HBTU (43 mg, 0.11 mmol). The reaction mixture was stirred at room temperature for 36 hours. DMF was removed by vacuum distillation and the residue was dissolved in MeOH (4 mL). The MeOH solution was filtered to remove the insolubles, the filtrate was concentrated in vacuo, and the residue was dissolved in a minimum amount of MeOH. $H_2O$ was then added to induce precipitation and the precipitate was dried on vacuum to give the titled compound (19 mg) (Yield: 42%).

The yield of the reaction was later improved by using EDC as the coupling reagent, as exemplified below. To a solution of compound YL-015-10 (40 mg, 0.054 mmol) and N-hydroxysuccinimide (13 mg, 0.115 mmol) in anhydrous DMF (3 mL), was added EDC (31 mg, 0.162 mmol). The solution was stirred at room temperature for 24 hours. DMF was removed by vacuum distillation and the residue was further dried on high vacuum. The residue was then dissolved in a minimum amount of MeOH (0.12 mL) and $H_2O$ (3.2 mL) was added to induce precipitation. The precipitates were washed with $H_2O$ (3×0.8 mL) and dried on vacuum to give a solid product (31 mg) (Yield: 69%). $^1$HNMR (MeOH-d4, 300 MHz).

8. Synthesis of Argatroban-C6 NHS Ester (compound YL-015-35). To a solution of compound YL-015-15 (78 mg, 0.12 mmol) and N-hydroxysuccinimide (29 mg, 0.25 mmol) in anhydrous DMF (6 mL) was added EDC (72 mg, 0.38 mmol). The solution was stirred at room temperature for 20 hours and DMF was removed by vacuum distillation. The residue was dissolved in a minimum amount of MeOH (0.4 mL) and $H_2O$ (1.2 mL) was added to induce precipitation. The precipitates were washed with $H_2O$ (3×0.7 mL) and dried on vacuum to afford a solid product. The solid product was furter purified by recrystallization from 20 acetone/ether (1/1, v/v) to give a white solid product (62 mg) (Yield: 69%). $^1$HNMR (MeOH-d4, 300 MHz).

9. Synthesis of Argatroban-C12 Sulfo-NHS Ester (compound YL-015-23). Compound YL-015-10 (10.0 mg, 13.5 μmol), sulfo-NHS (6.2 mg, 28.3 μmol) and EDC (8.2 mg, 42.5 μmol) were dissolved in anhydrous DMF (0.8 mL). The reaction mixture was stirred at room temperature for 2 days and DMF was removed by vacuum distillation. The residue was washed with a small amount of $H_2O$, then with EtOAc and acetone, to give a white solid product (9.2 mg) (Yield: 77%). $^1$HNMR (MeOH-d4, 300 MHz).

Results: A one-step derivatization of the thrombin inhibitor argatroban with a linking polypeptide and a chemically reactive group has been realized. Briefly, the free carboxylate group on the argatroban molecule is activated with HBTU, presumably via formation of N-hydroxybenzotriazole ester, which then reacts with the amino group of the linking polypeptide to give the desired adduct. A side-product with a molecular weight corresponding to that of argatroban minus a water molecule, was also observed by mass spectroscopic analysis. This by-product is probably derived from an internal nucleophilic attack on the activated ester. If the argatroban molecule was pre-activated with HBTU before the addition of the nucleophilic amino ester, more of the side product would be produced. Therefore, the amino ester and argatroban were mixed prior to addition of HBTU in the reaction. The product was purified on preparative TLC plates. Although the yields are relatively low (28–53%), the simple one-step linking polypeptide placement without protecting those functional groups on argatroban is very satisfactory.

Two amino aliphatic acid methyl esters with 6 and 12 methylene units spans were chosen as the linking polypeptides because of their structural stability and simplicity. The linking polypeptides of variable lengths will provide information on length requirement for optimal drug presentation to its target.

Subsequent hydrolysis of the methyl esters on the linking polypeptides under alkaline condition went smoothly to give the corresponding acid in 73–85% yields. Treatment of the free acid with HBTU in the presence of N-hydroxysuccininide and DIEA afforded the desired NHS ester in 42% yield. The yield was later improved to 69% by using EDC as the coupling reagent. The formation of the NHS ester was confirmed by $^1$HNMR and mass spectroscopy.

EXAMPLE 2

Derivatized Argatroban Molecules are Bioavailable after Covalent Attachment to Rabbit Erythrocytes Material and Methods: Rabbit erythrocytes were conjugated with the Argatroban-C6 NHS ester compound (compound YL-015-35). To do so, rabbit erythrocytes were isolated from fresh, citrated blood. In brief, an aliquot of blood was centrifuged for 5 minutes at 1800 rpm (Sorvall RC-5B, SH-3000 rotor). The buffy coat was pipetted off the top layer of the cell pellet and the remaining erythrocytes were washed four times with PBS, pH 7.4. Before the last wash, an aliquot of cells was removed for counting. The washed erythrocytes were resuspended at a density of $1\times10^9$ cells/mL. The total volume of cells labeled per sample was 3 mL. Cells were reacted at room temperature for 45 minutes with gentle agitation with one of the following reagents: (1) sham, 0.5% DMSO/PBS; (2) 100 μM argatroban C6-free acid (compound YL-015-15) in 0.5% DMSO/PBS; (3) 10 μM argatroban C6-NHS ester (compound YL-015-35) in 0.5% DMSO/PBS; (4) 50 μM argatroban C6-NHS ester (compound YL-015-35) in 0.5% DMSO/PBS; (5) 100 μM argatroban C6-NHS ester (compound YL-015-35) in 0.5% DMSO/PBS; and (6) 100 μM sulfo-NHS-LC-biotin (Pierce, catalog no. 21335) in 0.5% DMSO/PBS. After the labeling reaction, the cells were centrifuged 4 minutes at 1800 rpm and the supernatant was discarded. The cells were resuspended in 10 ml of 0.5% DMSO/PBS and pelleted. The cells were washed one more time with 10 ml of PBS.

To quench any remaining reactive esters, the cells were then resuspended in 6 mg/mL BSA/PBS (Sigma, A-2934, lot 93HO291) and gently agitated at room temperature for 30 minutes. After quenching, the cells were washed five times with PBS. Cell yields were determined by cell counting.

After conjugation, the cells were hypotonically lysed and the ensuing membrane (ghost) and cytosol fractions were assayed by immunoblotting and ELISA. Specifically, conjugated erythrocyte pellets were chilled on ice for 5 minutes. Cells were then lysed on ice with 12 ml of ice-cold 5 mM phosphate buffer, pH 8.0 (PB) containing 1 mM Pefabloc and 40 μM leupeptin. Lysates were briefly vortexed and then centrifuged for 20 minutes at 4° C. at 15,000 rpm (SS-34, Sorvall RC-5B). The supernatant (hemolysate) was pipetted off the pellet, labeled and stored at 4° C. The pellets (ghosts) were washed four times with 12 ml of cold PBS and centrifuged as above. The protein content of the ghosts and hemolysates was determined by using the Micro BCA kit (Pierce; catalog no. 23231). Cell fractions were stored at −80° C.

Samples were then solubilized in 2×reducing cocktail (5% SDS, 50% glycerol, 0.5 M 2-mercaptoethanol in 0.25 M Tris-HCl, pH 6.8). After a 5 minute treatment at 100° C. and then brief cooling, samples were resolved by SDS-PAGE on 10% polyacrylamide mini-gels. After electrophoretic transfer to nitrocellulose and brief Ponceau S staining, the blots were blocked with Blotto (5% instant non-fat dry milk in PBS, pH 7.4) for 2 hours at room temperature. The blots were then washed four times with TBS-T (20 mM Tris-HCl, pH 7.6, 137 mM NaCl, 0.25% Tween-20) and incubated for 2 hours at room temperature with a 1:1000 dilution of rabbit serum in TBS-T. Blots were then washed four times with TBS-T as above and incubated with biotinylated anti-rabbit IgG antibodies (Vector, BA-1000) for 1 hour at room temperature. Blots were washed as above and then were incubated with ABC-HRP (Vector) for 30 minutes at room temperature. After washing, blots were visualized with the metal enhanced DAB substrate kit (Pierce, catalog no. 34065).

Results: The results of the above described experiments demonstrated that numerous erythrocyte membrane proteins were covalently modified with the derivatized argatroban-C6 NHS ester molecule. By contrast, the presence of derivatized argatroban molecules on cytosolic proteins was at the limit of detection, suggesting that this thrombin inhibitor compound is an effective reagent for covalently bonding to proteins located on the outside of cells and, ultimately, for the delivery of drugs. Moreover, by a capture ELISA assay, it was observed that a portion of the thrombin inhibitor-labeled proteins belong to the glycophorin family of proteins.

EXAMPLE 3

Mass Spectrometric Analysis of Derivatized Argatroban Conjugation to Human Serum Albumin (HSA) and Rabbit Serum Albumin (RSA).

Materials and Methods: Mass spectrometry was used to support covalency of the bonding of derivatized argatroban molecules to the proteins human serum albumin (HSA) and rabbit serum albumin (RSA) as well as to quantitate the number of conjugated argatroban molecules covalently bound to the proteins. All samples were analyzed using a high performance liquid chromatograph (HPLC) coupled in-line to an electrospray ionization (ESI) mass spectrometer (MS) which is termed HPLC/ESIMS. Some samples were also analyzed using a matrix-assisted laser desorption ionization (MALDI) time-of-flight (TOF) mass spectrometer which is termed (MALDI-TOFMS).

Samples for HPLC/ESIMS were either prepared as duplicate reaction samples or were part of the same reaction samples which were used in the ELISA assays described below. These samples were injected directly only the HPLC/ESIMS without any manipulation other than dilution with water, where the PBS, DMSO, and unreacted derivative molecules are separated from the protein-argatroban derivative molecule conjugate. Samples for MALDI-MS were first HPLC-purified and mixed 1:1 directly on the stainless steel analysis plate with a matrix of 10 mg/ml sinnapinic acid in 50% acetonitrile/50% water. The mixture was then dried with a gentle flow of air to allow for crystallization and inserted into the instrument for laser ionization.

The HPLC is a Hewlett Packard 1090 Series II liquid chromatogram with a diode array detector. The column used for separation is a Brownlee aquapore OD-300 reversed phase C18 column, 1 mm×10 cm, 300 Å pore size, 7 μm particle diameter. The mass spectrometer to which the HPLC is connected using fused Silica capillary tubing is a Sciex API-300 triple quadrupole mass spectrometer with an ionspray source to allow for atmospheric pressure ionization of a liquid flowing continuously into the instrument. The MALDI-TOFMS is a Perceptive Biosystems Voyager Elite DE instrument run in the linear mode.

Results:

(1) Argatroban-C6 NHS Ester vs. Argatroban-C12 NHS Ester, 20:1 Molar Excess of Ester vs. HSA or RSA.

HPLC/ESIMS of HSA (0.33 μg/μl, 5 μM) reacted for 1 hour at room temperature with 100 μM argatroban-C6 NHS ester (compound YL-015-35) indicated a covalent addition of 1–8 argatroban derivative molecules per HSA molecule. RSA (0.30 μg/μl, 4.5 μM) reacted for 1 hour at room temperature with 100 μM argatroban-C6 NHS ester (compound YL-015-35) also indicated a covalent addition of 1–8 argatroban derivative molecules per RSA molecule. However, with the argatroban-C12 NHS ester (compound YL-015-11) under the same conditions, only 1–5 argatroban derivatives are covalently added per molecule of HSA or RSA. These results suggest that the argatroban derivative molecule having a linking polypeptide of 6 carbon atoms acts to provide more efficient bonding to available reactive functionalities on both HSA and RSA than does an argatroban derivative molecule having a linking polypeptide of 12 carbon atoms.

(2) HSA vs. RSA, Argatroban-C12 NHS Ester. 1:10 Molar Deficiency of Ester vs. Protein.

HPLC/ESIMS of HSA (0.33% μg/μl, 5 μM) reacted for 1 hour at room temperature with 0.5 μM argatroban-C12 NHS ester (compound YL-015-11) indicated a covalent addition of 0–4 argatroban derivative molecules per HSA molecule. RSA (0.30 μg/μl, 4.5 μM) reacted for 1 hour at room temperature with 0.5 μM argatroban-C12 NHS ester (compound YL-015-11) indicated a covalent addition of 0–3 argatroban derivative molecules per RSA molecule, or slightly less covalent labeling than obtained with the HSA protein.

(3) 15 μM vs. 30 μM RSA, Argatroban-C6 NHS Ester, 10-12:1 Molar Excess of Ester vs. RSA.

HPLC/ESIMS of RSA (1.0 μg/μl, 15 μM) reacted for 1 hour at room temperature with 200 μM argatroban-C6 NHS ester (compound YL-015-35) indicated a covalent addition of 1–9 argatroban derivative molecules per RSA molecule. RSA (2.0 μg/μl, 30 μM) reacted for 1 hour at room temperature with 300 μM argatroban-C6 NHS ester (compound YL-015-35) also indicated a covalent addition of 1–9 argatroban derivative molecules per RSA molecule. These results were confirmed by MALDI-MS analysis of these two samples which gives a single broad peak centered on the average molecular weight of the sample. Based on these average molecular weights, the 15 μM/200 μM RSA/argatroban derivative sample yielded an average of 5.6 argatroban derivative molecules added per RSA molecule (range of 1–10 added) and the 30 μM/300 μM RSA/argatroban derivative sample yielded an average of 5.4 argatroban derivative molecules added per RSA molecule (range of 1–10 added).

(4) Concentration Study of 1–100 μM Arzatroban-C6 NHS Ester Reacted with 4.5 μM RSA.

HPLC/ESIMS of RSA (0.30 μg/μl, 4.5 μM) reacted for 1 hour at room temperature with argatroban-C6 NHS ester (compound YL-015-35) (1, 10, 15, 20, 25, and 100 μM) yielded a linear covalent addition of argatroban derivative molecules to each molecule of RSA as indicated by the following results:

1 μM adds no detectable argatroban derivative molecules

10 μM adds 1 argatroban derivative molecule to ~50% of the RSA molecules

15 μM adds 0–3 argatroban derivative molecules per RSA molecule (majority of RSA molecules are +1)

20 μM adds 1–3 argatroban derivative molecules per RSA molecule (majority of RSA molecules are +1 and +2)

25 μM adds 1–4 argatroban derivative molecules per RSA molecule (majority of RSA molecules are +1 and +2)

100 μM adds 2–10 argatroban derivative molecules per RSA molecule (no major species).

EXAMPLE 4

Sandwich ELISA Assays to Assess the Relative Bioavailability of Derivatized HSA to Thrombin Materials and Methods: Human serum albumin (ISA, Sigma Cat. #A-8763) at a concentration of 333 μg/ml or rabbit serum albumin (RSA, Sigma Cat #A-9438) at a concentration of 300 μg/ml was reacted with 100 μM argatroban-C6 or -C12 NHS ester (compounds YL-015-35 or YL-015-11, respectively) in PBS, pH 7.4, for 1 hour at room temperature. The reaction was quenched by the addition of hydroxylamine, pH 7.8 to a final concentration of 50 mM and incubation at room temperature for 10 minutes. Prequenched negative control samples were of the same composition except that the argatroban NHS ester was reacted with hydroxylamine for 10 minutes prior to the addition of HSA or RSA. Finally, the HSA or RSA only sample had DMSO added to 1% to mimic the addition of argatroban NHS ester solutions and was incubated and quenched the same as the other reactions.

Rabbit anti-HSA (Boehringer/Mannheim, catalog no. 605001) or goat anti-RSA (Cappel, catalog no. 55629) antibodies were diluted 1:5000 in PBS, pH 7.4 and 100 μl/well was aliquotted into a NUNC Maxisorp F96 plates (catalog no. 439454). The plate was incubated overnight at 4° C., then blocked by the addition of 200 μl/well of 1% BSA/PBS and incubated at room temperature for 1 hour. The plate was then washed 5 times by submersion in PBS, pH 7.4.

The various HSA/argatroban derivative or RSA/argatroban derivative samples were serially diluted in 1% BSA/PBS (1:100 to 1:50,000) and 100 μl/well was added to duplicate wells of each sample dilution. Samples were incubated on the plates for 2 hours at room temperature and the plates were then washed as above.

Thrombin (Via Enzymes Systems, 11.4 mg/ml) was diluted to 9.4 μg/ml in PBS, pH 7.4, with 0.1% BSA/0.1% PEG 8000 (Sigma, catalog no. P-2139) and 100 μl/well was added. The plates were incubated at room temperature for 1 hour and washed as above.

Mouse anti-thrombin (American Diagnostics, catalog no. EST-7), an antibody thought to bind away from the active site of thrombin, was diluted to 1 μg/ml in PBS, pH 7.4, with 0.1% BSA/0.1% PEG 8000 and 100 μl/well was added to all wells. The plates were incubated at room temperature for 30 minutes and washed as above.

Biotinylated rabbit anti-mouse IgG (mouse gamma specific, Zymed, catalog no. 61-6540) was diluted 1:1000 in PBS, pH 7.4, with 0.1% BSA and 1% PEG 8000 and 100 μl/well was added to all wells. The plates were incubated at room temperature for 30 minutes and washed as above.

Next, 100 μl/well of ABC-HRP (Vector, catalog no. PK4000) was added, each component diluted 1:500 in PBS, pH 7.4, with 0.1% TWEEN 20 and incubated 30 minutes at room temperature prior to use. PEG 8000 was added to 0.1% just before addition of ABC-HRP to the plates. The plates were incubated with ABC-HRP for 30 minutes at room temperature and were then washed 10 times by submersion in PBS, pH 7.4.

Alternatively to adding biotinylated rabbit anti-mouse IgG and the ABC-HRP, the assay was simplified and background reduced by adding goat anti-mouse IgG conjugated with HRP (Jackson ImmunoResearch, catalog no. 115-035-146) diluted 1:500 in HRP diluent Medix, catalog no. RIH4203) and 100 μl/well added. The plates were incubated at room temperature for 30 minutes and were then washed 10 times by submersion in PBS, pH 7.4, Finally, 100 μl/well of o-phenylenediamine dihydrochloride (OPD, Sigma, catalog no. P-3804) was added at 0.5 mg/ml in citrate-phosphate buffer, pH 5.3 with 0.015% $H_2O_2$ and incubated at room temperature for 30 minutes. After incubation, 200 μl/well of 2 N sulfuric acid (VWR, catalog no. VW3S00-1) was added and absorbance was read at $OD_{490}$ in a SpectraMax plate reader (Molecular Devices) after agitating the plate for 5 seconds.

Results: The results obtained from the above sandwich ELISA assays are presented in FIGS. 2, 3 and 4. The data presented in FIG. 2 demonstrates that there is a significant increase of $OD_{490}$ in wells incubated with samples containing HSA reacted with argatroban-C6 or -C12 NHS ester (compounds YL-015-35 and YL-015-11, respectively) as compared to samples containing prequenched argatroban NHS ester or HSA alone. A significant signal above background was detected at approximately 10 ng/ml for both the C6 and the C12 derivatized compounds but the absolute signals for the two compounds are very different with the C6 having a significantly higher OD (approx 6–7 fold at saturation). These data suggest that the argatroban NHS ester derivative molecules have covalently bound to the HSA protein in such a way that it is able to interact and bind with thrombin which, inturn, can then be detected by an anti-thrombin antibody. These data, therefore, suggest that the argatroban derivatives covalently bound to the HSA protein is capable of binding to and inhibiting thrombin.

In the case of RSA, only the argatroban-C6 NHS ester derivative has been detected in an ELISA format (see FIG. 3). A significant signal above background was detected at approximately 30 ng/ml for the argatroban-C6 derivative. In this assay, the absolute signal is lower than that obtained with HSA. This maybe the result of differences in the assay due to the capture antibody, to differences in the extent and availability of labeling, or both.

Covalency of the bond between the argatroban NHS ester and the HSA or RSA protein was supported by mass spectrometry data (obtained from the duplicate reaction samples or the rest of the same reaction sample, described above) that showed that the argatroban derivative molecules had created covalent adducts on the majority of the HSA or RSA proteins present in the samples.

Human glycophorin A protein (hGPA) has also been reacted with the argatroban-C6 NHS ester derivative (compound YL-015-35) under similar conditions as for the RSA protein described above. The results of these studies are presented in FIG. 4. As is shown in FIG. 4, the hGPA protein reacted with the argatroban-C6 NHS derivative and was shown by ELISA to bind thrombin to give a detectable signal at approximately 30 ng/ml. The ELISA assay was identical to the one described for HSA and RSA above with the exception that mouse anti-hGPA (BioAtlantic/CRTS, mAb 5F4), diluted to 10 $\mu$g/ml in 0.1 M sodium acetate, pH 4.5, was used to capture the NHS-argatroban derivative reacted hGPA protein.

The results of the above experiments clearly demonstrate that the argatroban derivative molecules of the present invention not only covalently bond to reactive functionalities on various vascular-associated proteins, but do so in a way not to inhibit the ability of the derivative molecule to bind to and inhibit thrombin.

Keyhole limpet cyanin (KLH, Sigma, catalog no. R-5755) has also been reacted with argatroban-C12 NHS ester (compound YL-015-11) under similar conditions as for the HSA protein described above. The KLH protein reacted with argatroban-C12 NHS ester (compound YL-015-11) was shown by ELISA assay to bind to thrombin and give a detectable signal at approximately 100 ng/ml. The ELISA assay was identical to the one described above for HSA and RSA above with the exception that rabbit anti-KLH (Cappel, catalog no. 55966) diluted 1:5000 in PBS, pH 7.4 was used to capture the NHS-argatroban derivative reacted KLH. Because of the extremely heterogeneous nature of the KLH preparation, it was not possible to analyze these samples by mass spectrometry. However, similar material (reaction containing KLH at 2 mg/ml and argatroban-C12 NHS ester at 3.3 $\mu$M) was used to generate polyclonal antibodies to the argatroban derivative, thereby confirming the covalent modification of the KLH protein.

EXAMPLE 5

Sandwich ELISA Assays Using Polyclonal Antibodies to Evaluate HSA. hGPA and Rabbit Erythrocyte Ghosts Conjugated with Argatroban-C6 NHS Ester Materials and Methods: Human serum albumin (HSA, Sigma catalog no. A-8763) or human glycophorin A (hGPA) protein at a concentration of 300 $\mu$g/ml was reacted with 100 $\mu$M argatroban-C6 NHS ester (compound YL-015-35) in PBS, pH 7.4, for 1 hour at room temperature. The reaction was quenched by adding hydroxylamine, pH 7.8 to a final concentration of 50 mM and incubating at room temperature for 10 minutes. Prequenched negative control samples were of the same composition except that the argatroban-C6 NHS ester derivative was reacted with hydroxylamine for 10 minutes prior to the addition of HSA or hGPA protein. Finally, the HSA or hGPA only samples had DMSO added to 1% to mimic addition of argatroban derivative solutions and was incubated and quenched the same as other reactions.

Rabbit anti-HSA monoclonal antibody (Boehringer/Mannheim, catalog no. 605001) diluted 1:5000 in PBS, pH 7.4 or mouse anti-hGPA monoclonal antibody (BioAtlantic/CRTS, mAb 5F4, diluted to 10 $\mu$g/ml in 0.1 M sodium acetate, pH 4.5 or mAb 3C10 diluted 1:500 or mAb 3E4 diluted 1:1000 in PBS, pH 7.4 - each antibody recognizes a different epitope of hGPA), were used to capture respective proteins by aliquotting 100 $\mu$l/well into a NUNC Maxisorp F96 plate (catalog no. 439454). The plates were incubated overnight at 4° C., were then blocked by the addition of 200 $\mu$l/well of 1% BSA/PBS and incubated at room temperature for 1 hour. The plates were then washed 5 times by submersion in PBS, pH 7.4.

The various HSA/argatroban derivative or hGPA/argatroban derivative samples were serially diluted in 1% BSA/PBS (1:100 to 1:50,000) and 100 $\mu$l/well was added to duplicate wells for each sample dilution. Samples were incubated on the plates for 2 hours at room temperature and then were washed as above.

Rabbit anti-KLH-argatroban antibody was diluted 1:500 or 1:1000 in 1% BSA/PBS, pH 7.4 and 100 $\mu$l/well added to each well. The plates were then incubated at room temperature for 30 minutes and washed as above.

Biotinylated goat anti-rabbit IgG (Vector, catalog no. BA1000) was diluted 1:1000 in 1% BSA/PBS, pH 7.4 and 100 $\mu$l/well added to all wells. The plates were incubated at room temperature for 30 minutes and washed as above.

Next, 100 $\mu$l/well of ABC-HRP (Vector, catalog no. PK4000) was added, each component diluted 1:500 in PBS, pH 7.4, with 0.1% TWEEN 20 and incubated 30 minutes at room temperature prior to use. The plates were then washed 10 times by submersion in PBS, pH 7.4.

Finally, 100 $\mu$l/well of o-phenylenediamine dihydrochloride (OPD, Sigma, catalog no. P-3804) was added at 0.5 mg/ml in citrate-phosphate buffer, pH 5.3 with 0.015% $H_2O_2$ and incubated at room temperature for 15 –20 minutes. Then, 100 $\mu$l/well of 2 N sulfuric acid (VWR, catalog no. VW3500-1) was added and absorbance read at $OD_{490}$ in a SpectraMax plate reader (Molecular Devices) after agitating the plate for 5 seconds.

Results: The results of the above described experiments are presented in FIGS. 5, 6, 7 and 8. Specifically, there was a significant increase of $OD_{490}$ in wells incubated with samples reacted with argatroban-C6 NHS ester (compound YL-015-35) as compared to samples containing prequenched argatroban-C6 NHS ester or protein alone. A significant signal above background was detected at approximately 13 ng/ml for HSA-argatroban derivative (see FIG. 5) and 12 ng/ml for hGPA-argatroban derivative (5F4 mAb, see FIG. 6). The other anti-hGPA monoclonal antibodies (3C10 and 3E4) also detected hGPA-argatroban derivatives, however, at lower levels (see FIGS. 7 and 8, respectively). These data confirm the thrombin/anti-thrombin results showing that the argatroban-C6 NHS ester has covalently bound to the HSA and hGPA proteins and, once bound, binds to thrombin.

Rabbit erythrocyte ghosts that had been prepared and reacted with 100 µM argatroban-C6 NHS ester (compound YL-015-35) were also shown to be positive in an plate ELISA format using the polyclonal anti-KLH-argatroban antibodies to detect (rabbit erythrocytes reacted with 50 µM argatroban-C6 NHS ester were also tested but the signal was much lower). Sham treated rabbit erythrocytes or rabbit erythrocytes treated with the argatroban-C6 free acid (compound YL-015-15) did not give a signal above background. The ELISA assay was similar to the one described above for the HSA and RSA proteins with the exception that either goat anti-rabbit erythirocyte (Cappel, catalog no. 55616) diluted 1:500 or mouse anti-hGPA (BioAtlantic, mAb 3C10) diluted 1, 100 in PBS, pH 7.4 were used to capture the argatroban-C6 NHS ester reacted rabbit erythrocyte ghosts. The argatroban-C6 NHS ester was then detected using the polyclonal anti-KLH-argatroban antibodies (1:1000) in the same manner as for the HSA and hGPA proteins above. As a positive control, hGPA labeled with argatroban-C6 NHS ester (same material as above) was included in both assays and detected by the goat anti-rabbit erythrocyte to 60 ng/ml and the mouse anti-hGPA to 30 ng/ml. Using the goat anti-rabbit erythrocyte to capture, rabbit erythrocyte/NHS-argatroban conjugate was detected to 1.6–3.2 µg/ml of total protein. Using the mouse anti-hGPA (mAb 3C10) to capture, rabbit erythrocyte/NHS-argatroban conjugate was detected at about 160 µg/ml of total protein.

These results indicate that the argatroban-C6 NHS ester derivative has covalently attached to the rabbit erythrocytes in a manner that is detectable using polyclonal anti-KLH-argatroban antibodies. Since the mouse anti-hGPA was successful with rabbit cells, this assay should also be able to detect argatroban-C6NHS ester that has covalently attached to human erythrocyte ghosts and whole cells. Moreover, because the goat anti-rabbit erythrocyte antibody was able to detect hGPA, it is likely that this reagent could be used for human erythrocyte ghosts and cells as well.

EXAMPLE 6

Detection of Thrombin Inhibitory Activity

A variety of assays were employed to detect the ability of argatroban derivatives to inhibit thrombin activity. Specifically, a Km-based chromogenic assay was first employed. Initially, a 1 mL total volume containing argatroban or a derivative thereof, 8 µM S-2238 (H-D-Phe-Pip-Arg-p-nitroaniline ● 2 HCl) as a substrate for thrombin-induced hydrolysis in 0.1% PEG, 1% DMSO in PBS, pH 7.2, 35° C. was initiated by the addition of 10 mU of thrombin from human plasma and the absorbance was measured for 10 minutes at 405 nm. Measurements at 405 nm are designed to detect the thrombin-induced liberation of p-nitroaniline from the S-2238 substrate. As such, an observed increase in absorbance at 405 nm directly correlates with an increase in hydrolysis of the substrate by thrombin. The results from these studies indicated that the $IC_{50}$ for underivatized argatroban was 20 nM, whereas the $IC_{50}$ for a C12-tethered carboxylate of argatroban was 150 nM.

Similar results were obtained in a Km-based 96-well formatted fluorogenic assay employing 25 µM N-t-Boc-β-Benzyl-Asp-Pro-Arg-7-Amido4-MethylCoumarin HCI as a hydrolysis substrate (total volume 250 µl, 25 µM substrate, in 0.1 mg/ml BSA, PBS in 1% DMSO initiated by addition of 2.5 mU of thrombin from human plasma and absorbance measured for 10 minutes at 460 nm). Form these studies, the $IC_{50}$ for underivatized argatroban was 6 nM, for a C12-tethered carboxylate of argatroban, about 80 nM, and for compound YL-015-15, a C6-tethered carboxylate of argatroban, about 50 nM.

In a Vmax-based assay, (total volume 250 µl, 200 µM S-2238 as hydrolysis substrate in 0.1% PEG, 1% DMSO in PBS, pH 7.2, 25° C. initiated with 40 mU of thrombin from human plasma and measured for 20 minutes at 405 nm) the $IC_{50}$ for underivatized argatroban was 250 nM. The $IC_{50}$ for a C12-tethered carboxylate of argatroban in this assay was about 5–8 µM. Argatroban derivatized with a C6 instead of a C12-tether had an $IC_{50}$ of 1.25 to 10 µM, depending on whether in free acid or methyl ester form.

Reaction conditions for conjugation of HSA with an NHS ester derivative of argatroban: 5 µM HSA was incubated with 235 µM of NHS ester of argatroban in 1.5 DMSO, 1.5% ethanol in PBS, pH 7.4 for 1.5 hours at room temperature. At this point, the unreacted ester in the sample was quenched by addition of 1.2 mM hydroxylamine and held at room temperature for 30 minutes. Conjugated HSA was desalted on a kwiksep column to remove any unbound forms of the argatroban derivative and concentrated using a centricon-10 column to approximately the initial reaction volume. Appropriate analogous procedures were followed for controls using 1) underivatized HSA protein and 2) HSA protein processed with prequenched argatroban NHS ester.

In a Km-based inhibition assay for thrombin from human plasma, 2.5 mU of thrombin in 10 µl of 0.1% polyethylene glycol 8000 (PEG) in PBS, pH 7.2, were added to 240 µl of PBS containing as final concentrations 10 µM S-2238 hydrolysis substrate, 1% DMSO, 0.1% PEG, and with or without 40 µg/ml HSA. HSA proteins tested included HSA conjugated with an NHS ester of argatroban, HSA processed with hydroxylamine prequenched NHS ester of argatroban and HSA processed through the same incubations and desaltings used to remove residual or free acid forms of the NHS ester of argatroban as in the above samples. The rate of substrate hydrolysis by thrombin was nearly linear for the first ten minutes in all cases, as measured by an increase in absorbance at 405 nm from the production of free p-nitroaniline. In duplicate wells 1) lacking HSA or 2) containing underivatized HSA or 3) containing HSA processed with quenched NHS ester of argatroban, the rate of hydrolysis of substrate was indistinguishable between samples and ranged from 0.94 to 1.08 mOD/minute. In duplicate wells containing HSA conjugated with the NHS ester of argatroban, the rate of hydrolysis of substrate ranged from 0.66 to 0.71 mOD/minute, thus, 32% inhibited compared to controls.

In a second independent experiment, HSA was again conjugated with argatroban-C12 NHS ester (compound YL-015-11). Controls containing HSA with prequenched NHS ester, or HSA alone, were also prepared. Samples were assayed in duplicate, and a concentration range of HSA of 20, 40, and 80 mg/ml tested. HSA conjugated with argatroban-C12 NHS ester inhibited thrombin activity from 35–42% at 80 mg/ml compared to control samples, with 15–20% inhibition at 40 mg/ml relative to control samples.

EXAMPLE 7

$K_m$-Based Fluorogenic Assay for Inhibition of Thrombin from Human Plasma

Thrombin from human plasma was obtained from Enzyme System Products, Dublin, Calif., in glycerol:water 1:1, 11.4 mg/ml, 3800 U/mg, MW 36,700, and stored undiluted at −20° C. It was freshly diluted the day of use.

To dilute for the assay, 0.67 μl (25 Units) of thrombin was pipetted into 5 ml of 0.1 mg/ml BSA (from Pierce, Catalog No. 23209, BSA fraction V, a 2 mg/ml stock in saline with sodium azide), in cold PBS (GIBCO, Catalog No. 14190-136, without calcium chloride and magnesium chloride, pH 7.2) and briefly vortexed, yielding a stock of 5 mU thrombin/μl. A second dilution of 250 μl of this stock into 9.75 ml of 0.1 mg BSA/ml PBS resulted in a 0.125 mU/μl, or 3.125 mU/25/μl, final working stock.

The substrate was N-tBOC-β-Benzyl-Asp-Pro-Arg-7-Amido4-Methylcoumarin HCl and was obtained from Sigma, Catalog No. B4028, Lot 122H0070, F.W. 770.3. Five mg was dissolved in 1.42 ml DMSO for a 4 mM stock. The stock was stored in 200 μl aliquots at −20° C. in the dark.

An alternative substrate was N-tBOC-Val-Pro-Arg-7-Amido4-Methylcoumarin HCl and was obtained from Sigma, Catalog No. B-9385, Lot 53H0805, F.W. of free base 627.7. Five mg was dissolved in 1.863 ml DMSO for a 4 mM stock. The stock was stored in 200 μl aliquots at −20° C. in the dark.

The fluorescent standard was 7-Amido4-Methylcoumarin and was obtained from Aldrich, Catalog No. 25,737-0, MW 175.19. 6.1 mg was dissolved in 1.743 ml of DMSO for a 20 mM stock. The stock was stored in 200 μl aliquots at −20° C. in the dark.

Assays were performed kinetically at ambient temperature (about 20° C.) in 96-well microtiter plates (Nunc Immunomodule Maxisorb, a flat bottomed polystyrene plate) on a Perseptive Biosystems Cytofluor I. Stock solutions containing common concentrations and components for each well or group of well were prepared and 200 μl aliquotted per microfiter well. Assays were routinely conducted in a total volume of 250 μl, which allows for 25 μl for inhibitor and 25,μl for thrombin (about 3 mU).

For an initial determination of $K_m$ and $V_{max}$, the concentration of the fluorogenic substrate N-tBOC-β-Benzyl-Asp-Pro-Arg-7-Amido4-Methylcoumarin was varied from 5 to 200 μM.

For inhibition assays, final concentrations per well (250 μl $V_T$) included 25 μM N-tBOC-β-Benzyl-Asp-Pro-Arg-7-Amido4-Methylcoumarin HCl (approximately $K_m$), 0.1 mg BSA/ml PBS, and 1% DMSO. Initial readings were taken to ensure exclusion of rogue wells with abnormally high backgrounds (λ excitation at 360 nM, bandwidth 40 nM, λ emission, 460 nm, bandwidth 40 nm). Then, 25 μl of a 10×stock of the putative inhibitor were added per well, mixed for 5 seconds and read kinetically for 10 minutes at ambient temperature to assess background interference and/or any increase in hydrolysis of substrate due to inhibitor.

In inhibition assays using argatroban or soluble, tethered variants of argatroban (C6 or C12), samples were dissolved in DMSO at 1 mM, then diluted appropriately for assay in 1% DMSO in the buffer specified above.

Derivatized argatroban molecules attached to RSA or ghosts derived from red blood cells by an activator were formulated in phosphate buffer. Additional RSA of ghost samples processed (1) with tethered argatroban molecules lacking activator or (2) with activator groups attached to ligands that do not inhibit thrombin were included as negative controls.

The thrombin assay was then initiated by adding 25 μl of thrombin/well with a multichannel pipettor and mixed for 5 seconds. The appearence of the fluorescent product (free 7-amido-4-methylcoumarin released from the peptide by thrombin) was followed simultaneously in 48 wells (one reading per minute for 30 minutes, λ excitation at 360 nm, bandwidth 40 nm, λ emission, 460 nm, bandwidth 40 nm). The velocity of the reaction was deterined as an initial velocity in the first 10 minutes, with the signal in relative fluorescent units (RFU) of an uninhibited reaction about 9,000–10,000, above an initial background reading of about 1,000 (gain setting of 80). Routinely, less than 5% of the initial substrate was converted to fluorescent product during 10 minutes, and samples and curves are run in duplicate. A standard curve of thrombin activity from 0.3125–3.5 mU/well was included, as well as a standard curve of 7-amido4-methylcoumarin (ranging from 5 to 200 pmoles/well in 1% DMSO, 0.1 mg BSA/ml PBS, $V_T$ 250 μl/well). The pH of each sample was verified as 7.2 with pH paper at the end of the assay.

The results of the above assays are shown in FIGS. 9 and 10. Specifically, FIG. 9 illustrates the ability of the RSA-argatroban (C6) conjugate to inhibit thrombin. The $IC_{50}$ for this conjugate was estimated to be 25 nM. By contrast, the control RSA sample was not inhibitory at any concentration assayed. This result confirmns that the C6-tethered argatroban molecules which are covalently-linked to the RSA protein are bioactive as well as bioavailable. Indeed, this observation was extended to erythrocyte ghosts which were labeled with the C6-tethered argaroban molecule (see FIG. 10). This graph illustrates a kinetic assay of increasing aliquots of ghosts derived from erythrocytes labeled with 100 μM argatroban (C6)-NHS ester. Control sham-treated ghosts or ghosts derived from cells treated with the corresponding argatroban C6-carboxylate were not inhibitory (data not shown). Taken together, these data demonstrate that carrier proteins, either cellularly- or non-cellularly-associated, when conjugated to tethered argatroban molecules are effective drug carriers and that this treatment maintains the bioactivity of the thrombin inhibitor.

EXAMPLE 8

Platelet Aggregation Assays

A thrombin-induced platelet aggregation assay was selected to further confirm the bioactivity of the tethered argatroban (C6)-RSA conjugates. The conjugate was prepared according to the following protocol. A 15 μM solution of RSA in PBS was reacted with 200 μM argatroban-C6 NHS ester for 1 hour at room temperature. Sham samples consist of the RSA incubated for the same length of time at RT in 2% DMSO in PBS. Each of the samples was then concentrated to a final volume of 1.5 mL using Amicon Centricon 30 filtration/concentration devices. The concentrated samples were then desalted on Pierce's 5 ML Kwiksep excellulose plastic desalting columns. The excluded volumes containing RSA or argatroban-C6-RSA were then subjected to BCA microprotein estimation and lyophilization. In addition, these samples were analyzed by LC/MS, sandwich ELISA assays (described above) to measure thrombin binding and immunoblotting. From LC/MS analysis, an average of 10 tethered argatroban molecules were conjugated to each RSA molecule.

Platelets were purified from freshly drawn human blood diluted with the anticoagulant buffer ACD (9 mls of blood to 1 mL of buffer). The blood was centrifuged for 25 min at 200×g. The platelet-rich plasma (PRP) was recovered with a plastic pipette. The PRP was centrifuged for 15 min at 3,000×g in v-shaped plastic tubes. The supernatant, called platelet-poor plasma (PPP), was then removed and saved, and the platelets were resuspended in buffer A1 (35 mM citric acid, 103 mM NaCl, 5 mM each of glucose and KCl, 2 mM $CaCl_2$, 1 mM $MgCl_3$, 3.5 mg/mL BSA, 0.1 μM PGE1 and 0.3 U/mL of apyrase at pH 6.5). The resuspended platelets were washed 2 times with buffer A1. After the last wash, the platelets were resuspended in buffer B1 (137 mM NaCl, 2.6 mM KCL 12 mM NaHCO$_3$, 0.3 mM NaH$_2$PO$_4$, 3 mM CaCl$_2$, 1 mM MgCl$_2$, 5 mM glucose, 3.5 mg/mL BSA and 0.05 U/nL apyrase at pH 7.4) at a density of 3×10$^5$/µL. The platelets were maintained at room temperature until ready for use.

Various parameters relevant to platelet aggregation were obtained on a four channel aggregometer manufactured by AFFI BIO. In brief, the reaction chambers are warmed to 37° C. and are agitated at a rate of 1,200 rpm. Light is passed through the reaction chambers, with 300 µL of buffer B1 used to set the 100% transmittance level for each chamber. From a series of standardization experiments, it was determined that 0.5 U/mL of human thrombin (Sigma) is an optimal aggregating concentration of thrombin and is used to set. the 0% transmittance for the instrument. Standard conditions for the assay involve incubating 250 µL of the platelet suspension with or without 50 µL of inhibitor diluted in buffer in the reaction chambers for 60 seconds at 37° C. The value of transmittance is now set as 0%. After this measurement, thrombin is added to the reaction chambers (20 µl) and transmittance is measured for the next 6 minutes. Samples were performed in triplicate.

FIG. 11 depicts the delay in thrombin-induced platelet aggregation affected by various titrations of RSA. By contrast to the sham-treated RSA, the argatroban-C6-RSA clearly delayed platelet aggregation.

Table 1 tabulates the estimated concentrations of the conjugates which inhibit 50% of the aggregation (IC$_{50}$).

TABLE 1

| Compound | IC$_{50}$ |
| --- | --- |
| Free argatroban | 0.1–0.15 µM |
| RSA-argatroban-C6 conjugate | 4.5–7.5 µM |
| RSA sham | >150 µM |

As shown in Table 1, using an average of 10 argatrobans/RSA and the known dilution of RSA in the samples, the estimated IC$_{50}$ value for the argatroban-C6-RSA was determined to be in the range of 4.5 to 7.5 µM. By contrast, the sham-treated RSA did not interfere with platelet aggregation even at 150 µM. Higher concentrations were not tested, so the IC$_{50}$ for the-sham RSA was not determined. The IC$_{50}$ for argatroban in this assay is approximately 0.1 µM, which is in line with literature values. This value is at least an order of magnitude more effective than the argatroban-C6-RSA conjugate. This trend was expected based on the increased IC$_{50}$ observed for the C6-tethered argatroban carboxylate as compared to argatroban in the earlier-described K$_m$-based fluorogenic thrombin inhibition assay.

It is evident from the above results that the subject invention provides for greatly improved treatment involving thrombin inhibition. By use of the subject invention, the conjugated thrombin inhibitors maintain for extended periods of time, so that repetitive dosages are not required, compliance by the patient is not required, and protection is ensured. The derivatized thrombin inhibitors of the present invention covalently attach to erythrocytes, plasma proteins and various other vascular components while retaining biological activity and are not immunogenic.

All publications and patent applications mentioned in this specification are herein incorporated by reference to the same extent as if each individual publication or patent application was specifically and individually indicated to be incorporated by reference.

The invention now being fully described, it will be apparent to one of ordinary skill in the art that many changes and modifications can be made thereto without departing from the spirit or scope of the appended claims.

What is claimed is:

1. A method of accelerating the dissolution of an existing thrombus in the cardiovascular system of a patient, comprising:

administering to said patient a compound of the formula:

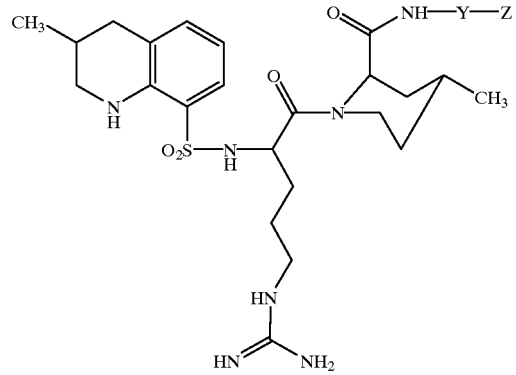

wherein:

Y is a linking group of from 2–30 atoms; and

Z is a chemically reactive group, or an activatable precursor to said chemically reactive group, for reaction in vivo with a reactive functionality of a component of said thrombus, or blood or blood vessel or arterial wall of said cardiovascular system to form covalent bonds linking the argatroban moiety of said formula therewith.

2. The method of claim 1 wherein said compound is administered intravascularly, intraarterially, intramuscularly, subcutaneously, orally, nasally, rectally, transdermally, or via an aerosol.

3. The method of claim 2 wherein said compound is administered intraarterially or intravascularly via a device wherein said device is selected from the group consisting of syringes, trocars and catheters.

4. The method of claim 3 wherein said compound is administered via a catheter.

5. The method of claim 4 wherein said compound is administered with said catheter at or near said thrombus.

6. The method of claim 1 wherein said component is a long-lived blood component.

7. The method of claim 6 wherein said long-lived blood component is an erythrocyte or a platelet.

8. The method of claim 1 wherein Y is an alkylene, oxyalkylene or polyalkylene group.

9. The method of claim 8 wherein said group has 6 or 12 carbon atoms.

10. The method of claim 1 wherein Z is a carboxy group, a carboxy ester group or a mixed anhydride.

11. The method of claim 10 wherein Z is selected from the group consisting of N-hydroxysuccinimide, isocyanate, thioester, thionocarboxylic acid ester, imino ester, carbodiimide anhydride, carbonate ester, phosphoryl ester and N-hydroxy sulfosuccinimide.

12. The method of claim 7 wherein said group has 6 carbon atoms and Z is N-hydroxysuccinimide.

13. A method for improving blood circulation in a patient by inhibiting the production of a thrombus in the cardiovascular system of said patient, comprising:

(a) preparing a pharmaceutical composition including a compound of the formula:

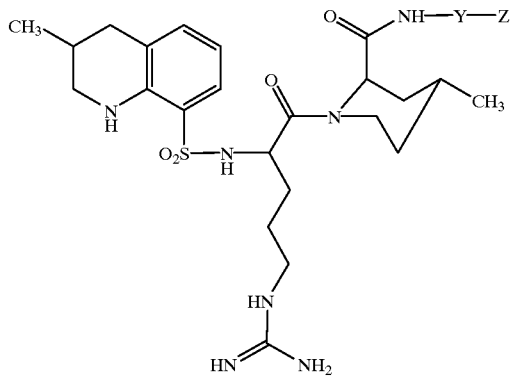

wherein:

Y is a linking group of from 2–30 atoms; and

Z is a chemically reactive group or an activatable precursor to said chemically reactive group for reaction in vivo with a reactive functionality of a target molecule to form covalent bonds therewith; and (b) administering said composition to said patient whereupon the argatroban moiety according to said formula is covalently linked to a blood vessel or arterial wall or to one or more long-lived blood components in the blood of said patient.

14. The method of claim 13 wherein said composition is administered after surgery.

15. The method of claim 13 wherein said composition is administered to said patient after said patient has suffered a myocardial infarction.

16. The method of claim 13 wherein said patient has a deep vein thrombosis.

17. The method of claim 13 wherein said patient has arteritis of the legs.

18. The method of claim 13 wherein Y is an alkylene, oxyalkylene or polyalkylene group.

19. The method of claim 18 wherein said group has 6 carbon atoms.

20. The method of claim 18 wherein said group has 12 carbon atoms.

21. The method of claim 13 wherein Z is a carboxy group, a carboxy ester group or a mixed anhydride.

22. The method of claim 13 wherein Z is selected from the group consisting of N-hydroxysuccinimide, isocyanate, thioester, thionocarboxylic acid ester, imino ester, carbodiimide anhydride, carbonate ester, phosphoryl ester and N-hydroxy sulfosuccinimide.

23. The method of claim 18 wherein said group has 6 carbon atoms and Z is N-hydroxysuccinimide.

* * * * *